United States Patent
Deshpande et al.

(10) Patent No.: US 10,815,461 B2
(45) Date of Patent: *Oct. 27, 2020

(54) RECOMBINANT URICASE ENZYME

(71) Applicant: Allena Pharmaceuticals, Inc., Newton, MA (US)

(72) Inventors: Aditi R. Deshpande, Newton, MA (US); Danica Grujic, Boston, MA (US); Sridhar Govindarajan, Los Altos, CA (US); Mark Welch, Fremont, CA (US)

(73) Assignee: Allena Pharmaceuticals, Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/674,325

(22) Filed: Nov. 5, 2019

(65) Prior Publication Data

US 2020/0071681 A1 Mar. 5, 2020

Related U.S. Application Data

(63) Continuation of application No. PCT/US2018/041015, filed on Jul. 6, 2018.

(60) Provisional application No. 62/678,511, filed on May 31, 2018, provisional application No. 62/529,726, filed on Jul. 7, 2017.

(51) Int. Cl.
| | |
|---|---|
| *C12N 9/06* | (2006.01) |
| *A61P 7/00* | (2006.01) |
| *A61K 38/44* | (2006.01) |
| *C12N 1/16* | (2006.01) |

(52) U.S. Cl.
CPC ............ *C12N 9/0048* (2013.01); *A61K 38/44* (2013.01); *A61P 7/00* (2018.01); *C12N 1/16* (2013.01); *C12Y 107/03003* (2013.01)

(58) Field of Classification Search
None
See application file for complete search history.

(56) References Cited

U.S. PATENT DOCUMENTS

| | | | |
|---|---|---|---|
| 5,700,674 A | 12/1997 | Koyama et al. | |
| 5,801,036 A | 9/1998 | Koyama et al. | |
| 6,576,235 B1 | 6/2003 | Williams et al. | |
| 6,783,965 B1 | 8/2004 | Sherman et al. | |
| 6,913,915 B2 | 7/2005 | Ensor et al. | |
| 7,723,089 B2 | 5/2010 | Williams et al. | |
| 7,927,589 B2 | 4/2011 | Williams et al. | |
| 7,927,852 B2 | 4/2011 | Sherman et al. | |
| 8,067,553 B2 | 11/2011 | Williams et al. | |
| 8,557,831 B2 | 10/2013 | Johnson et al. | |
| 8,618,267 B2 | 12/2013 | Williams et al. | |
| 8,921,064 B2 | 12/2014 | Sherman et al. | |
| 9,155,740 B2 | 10/2015 | Johnson et al. | |
| 9,377,454 B2 | 6/2016 | Rosario-Jansen et al. | |
| 9,534,013 B2 | 1/2017 | Fischer et al. | |
| 9,885,024 B2 | 2/2018 | Williams et al. | |
| 10,139,399 B2 | 11/2018 | Rosario-Jansen et al. | |
| 2017/0258927 A1 | 9/2017 | Johnston | |
| 2018/0223263 A1 | 8/2018 | Sherman et al. | |
| 2018/0282707 A1 | 10/2018 | Jiang et al. | |
| 2018/0289776 A1 | 10/2018 | Johnston | |
| 2019/0317083 A1 | 10/2019 | Rosario-Jansen et al. | |
| 2020/0056160 A1 | 2/2020 | Fischer et al. | |

FOREIGN PATENT DOCUMENTS

| | | | |
|---|---|---|---|
| WO | WO-2018089808 A1 | 5/2018 | |
| WO | WO-2020052457 A1 | 3/2020 | |

OTHER PUBLICATIONS

Li, W.L., et al. 2017 PloS One 12(5): e0177877 (18 pages). (Year: 2017).*
Arnold, F.H. 2001 Nature 409: 253-257. (Year: 2001).*
Fels and Sundy (2008) Curr. Opin. Rheumatol., 20(2): 198-202.
International Search Report for PCT/US2018/041015, dated Sep. 26, 2018 (4 pages).
Liu et al. (2011) Appl. Microbiol. Biotechnol., 92(3): 529-37.
Truszkowski, et al. (1935) Biochemical Journal, 29(12): 2787-2797.
Wiederkehr et al. (2011) Clin. Rev. Bone. Miner. Metab., 9(3-4): 207-217.
Written Opinion for PCT/US2018/041015, dated Sep. 26, 2018 (7 pages).
Wu et al. (1994) Proc. Nat. Acad. Sci. USA, 91: 742-746.

* cited by examiner

*Primary Examiner* — Marsha Tsay
(74) *Attorney, Agent, or Firm* — Goodwin Procter LLP

(57) ABSTRACT

Disclosed are recombinant mutant *Candida utilis* uricase enzymes with improved pancreatin stability and/or activity, compositions containing such uricase enzymes, which can be used, among other things, to treat diseases or disorders associated with an elevated amount of uric acid, including, for example, hyperuricemia, hyperuricosuria, and gout.

30 Claims, 10 Drawing Sheets

Specification includes a Sequence Listing.

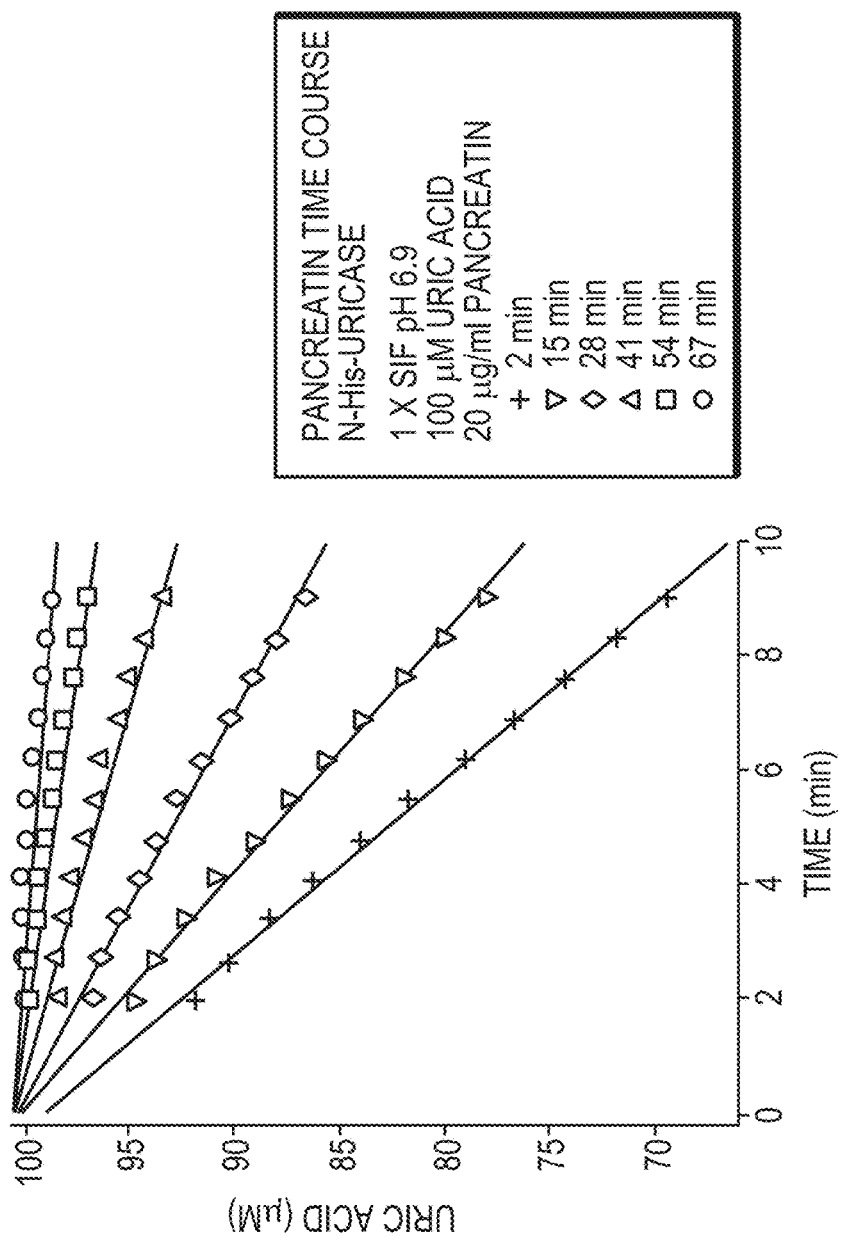
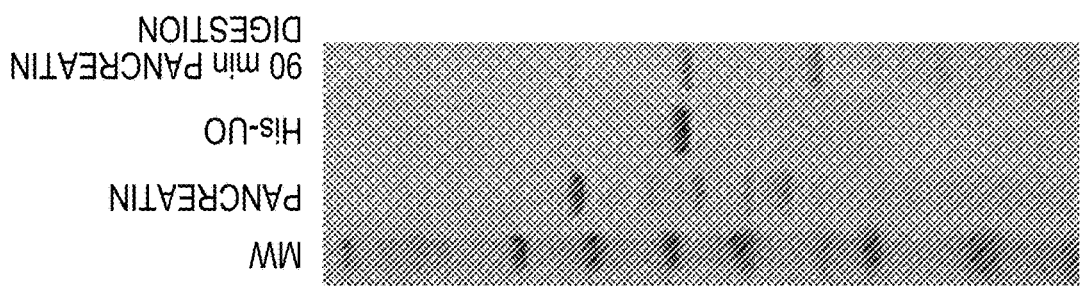
FIG. 1B
FIG. 1A

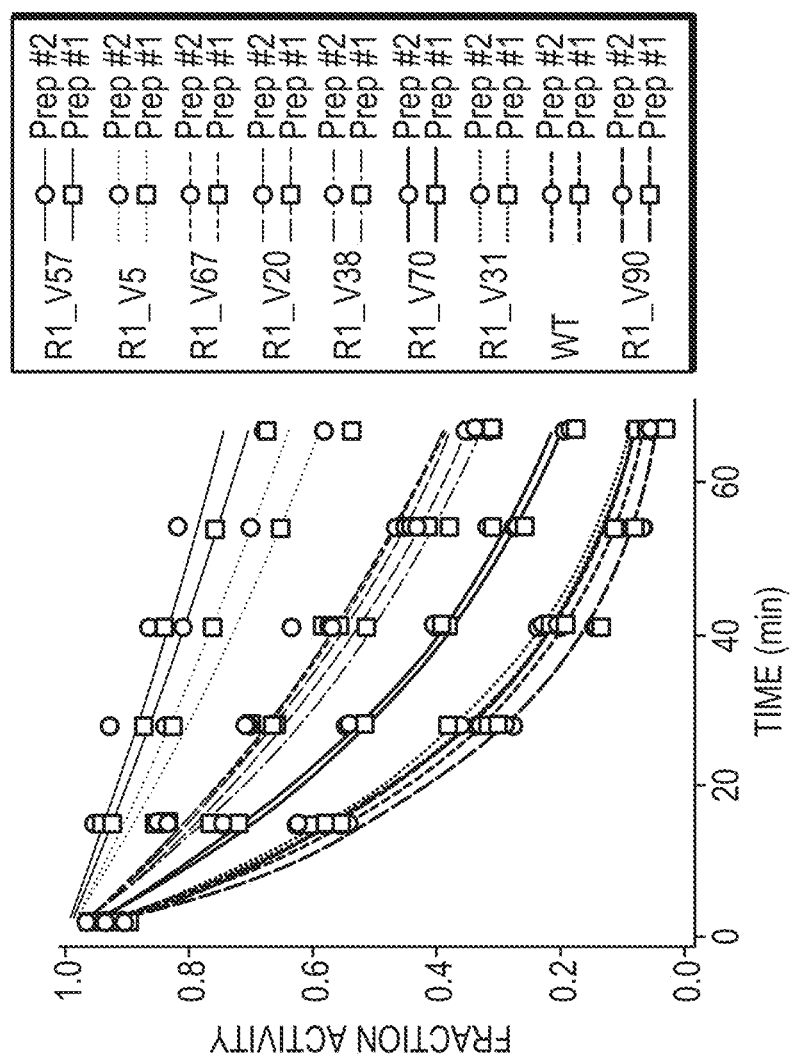
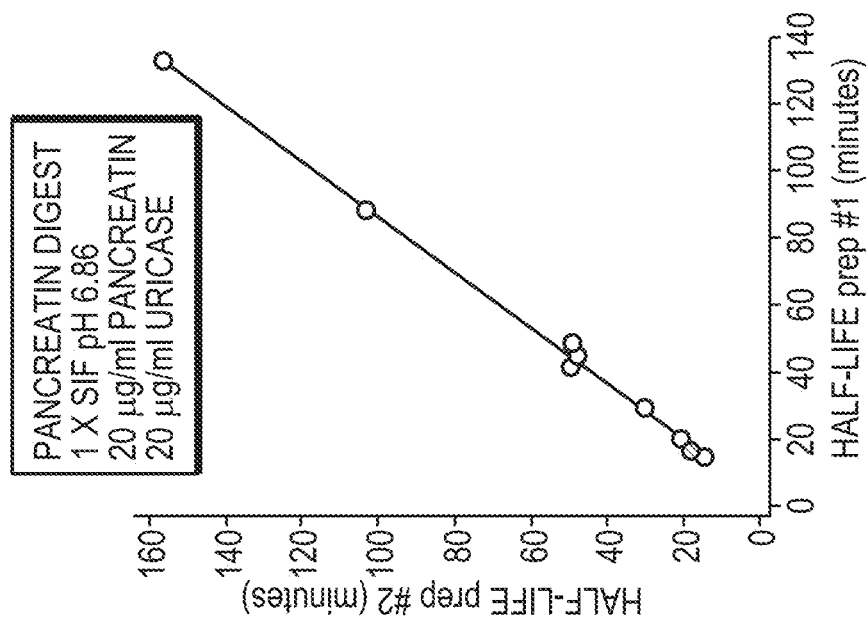
FIG. 2A
FIG. 2B

RECOMBINANT URICASE ENZYME

CROSS-REFERENCE TO RELATED APPLICATIONS

This application is a continuation of International Patent Application No. PCT/US2018/041015, filed Jul. 6, 2018, which claims the benefit of and priority to U.S. application No. 62/529,726, filed Jul. 7, 2017, and U.S. application No. 62/678,511, filed May 31, 2018, the contents of each of which are hereby incorporated by reference in their entireties for all purposes.

FIELD OF THE INVENTION

The invention relates generally to methods and compositions for treating diseases or disorders associated with an elevated amount of uric acid, and, more particularly, the invention relates to recombinant mutant *Candida utilis* uricases and methods using, and compositions containing, such uricases for treating diseases or disorders associated with an elevated amount of uric acid.

BACKGROUND

Uric acid is the final oxidation product of purine metabolism in humans and higher primates. Uricase, or urate oxidase, is an enzyme that degrades uric acid into allantoin and carbon dioxide. Due to mutational silencing, humans and higher primates lack a functional uricase gene. Therefore, unlike certain other mammals, humans have lost the capacity to metabolize uric acid by hepatic uricase due to mutational silencing of the enzyme. Although humans produce large quantities of uric acid, the majority of the uric acid is excreted in urine. Nevertheless, increased production and/or decreased excretion of uric acid can result in high levels of uric acid in blood (hyperuricemia) and urine (hyperuricosuria). Hyperuricemia and hyperuricosuria can result, for example, as in inflammatory arthritis due to urate deposits in joints and cutaneous tissue.

Gout is a condition that affects an estimated 8 million Americans and is characterized by recurring attacks of joint inflammation (arthritis). The joint inflammation is precipitated by deposits of uric acid crystals in the joint fluid (synovial fluid) and joint lining (synovial lining). Intense joint inflammation occurs as white blood cells engulf the uric acid crystals and release inflammatory chemicals, causing pain, heat, and redness of the joint tissues. Chronic gout can additionally lead to decreased kidney function and kidney stones.

Limitations in efficacy and/or tolerance of existing therapies of gout such as oral xanthine oxidase inhibitors (for example, allopurinol), uricosurics, and intravenous uricase agents, contribute to refractoriness to urate-lowering therapy (ULT) in gout. For example, delayed or insufficient dosing with allopurinol contributes to refractory gout. See Fels and Sundy (2008), CURR. OPIN. RHEUMATOL., 20(2): 198-202. Renal excretion is the major route of uric acid elimination, but the gastrointestinal tract (GIT) plays an increasingly recognized role in urate homeostasis, especially in chronic kidney disease (CKD) where urate renal elimination is impaired.

Functional uricase enzymes can be found in a wide range of organisms, including animals, plants, bacteria and fungi, and, as such, exogenous uricase has been used in the treatment of diseases or disorders associated with an elevated amount of uric acid. Clinically approved uricases include Krystexxa® (pegloticase), which has been approved for the treatment of chronic refractory gout, and Elitek® (rasburicase), which has been approved for tumor lysis syndrome.

Although developments have been made to date, there is still an ongoing need for new and effective therapies for treating and managing diseases or disorders associated with an elevated amount of uric acid such as hyperuricemia and gout, and improved uricase enzymes for use in treating and managing such diseases or disorders.

SUMMARY OF THE INVENTION

The invention is based, in part, upon the discovery of recombinant uricase enzymes that are active in humans and have greater stability and/or activity than naturally occurring enzymes. In particular, the recombinant enzymes of the invention exhibit improved stability against proteolytic digestion by pancreatin (a collection of enzymes secreted by the pancreas) compared to naturally occurring versions of the enzyme. Furthermore, the recombinant enzymes of the invention may have greater specific activity than a wild type uricase enzyme. Furthermore, it is contemplated that the recombinant enzymes described herein, given their enhanced stability, may be suitable for oral administration, and therefore potentially safer and more tolerable than the commercially available, injectable forms of uricase (e.g., Krystexxa® and Elitek®), because it is contemplated that the enzymes will remain active within the intestines and will not be absorbed through the intestinal wall.

In one aspect, the invention provides a recombinant mutant *Candida utilis* uricase enzyme that comprises at least one (for example, one, two, three, four, five, six, seven or eight) mutation(s) at a position corresponding to wild type *C. utilis* uricase of SEQ ID NO: 1, wherein the at least one mutation is selected from: (a) at position 180, isoleucine is substituted by valine or alanine (I180V or I180A), (b) at position 165, tyrosine is substituted by phenylalanine (Y165F), (c) at position 190, valine is substituted by glycine or alanine (V190G or V190A), (d) at position 51, glutamic acid is substituted by lysine (E51K), (e) at position 244, glutamine is substitute by lysine (Q244K), (f) at position 132, isoleucine is substituted by arginine or asparagine (I132R or I132N), (g) at position 97, valine is substituted by isoleucine (V97I), (h) at position 92, glutamic acid is substituted by asparagine (E92N), (i) at position 87, alanine is substituted by glycine (A87G), (j) at position 142, aspartic acid is substituted by glutamic acid (D142E), (k) at position 44, glycine is substituted by alanine (G44A), (l) at position 128, glycine is substituted by proline (G128P), (m) at position 236, alanine is substituted by asparagine (A236N), (n) at position 208, lysine is substituted by alanine (K208A), (o) at position 213, asparagine is substituted by alanine (N213A), (p) at position 140, serine is substituted by threonine (S140T), (q) at position 253, tyrosine is substituted by glutamine (Y253Q), (r) at position 84, alanine is substituted by serine (A84S), (s) at position 47, threonine is substituted by glutamic acid (T47E), (t) at position 95, serine is substituted by proline (S95P), (u) at position 103, lysine is substituted by threonine (K103T), (v) at position 134, aspartic acid is substituted by glutamic acid (D134E), (w) at position 136, tyrosine is substituted by arginine (Y136R), (x) at position 196, isoleucine is substituted by leucine (I196L), (y) at position 224, threonine is substituted by aspartic acid (T224D), (z) at position 285, proline is substituted by serine (P285S), and (aa) at position 296, valine is substituted by alanine (V296A).

In certain embodiments, the recombinant mutant *C. utilis* uricase enzyme comprises at least one mutation selected from: I180V, I180A, Y165F, V190G, V190A, E51K, Q244K, I132R, V97I, E92N, A87G, D142E, G44A, G128P, A236N, K208A, N213A, S140T, Y253Q, and A84S. In certain other embodiments, the uricase enzyme comprises at least one mutation selected from: I180V, I180A, Y165F, V190G, E51K, Q244K, I132R, V97I, E92N, A87G, D142E, and G44A. In certain other embodiments, the uricase enzyme comprises at least one mutation selected from: I180V, I180A, Y165F, V190G, E51K, I132R, and G44A. In certain other embodiments, the uricase enzyme comprises at least one mutation selected from: I180V, I180A, Y165F, E51K, I132R, and G44A. In certain other embodiments, the uricase enzyme comprises at least one mutation selected from: I180V, I180A, Y165F, V190G, E51K, Q244K, and I132R.

In another aspect, the invention provides a recombinant mutant *C. utilis* uricase enzyme comprising at least one (for example, one, two, three, four, five, or six) mutation(s) at a position corresponding to wild type *C. utilis* uricase of SEQ ID NO: 1, wherein the at least one mutation is present at a position selected from position 180, position 165, position 190, position 51, position 132, and position 44. In certain embodiments, one or more mutations may be conservative substitutions relative to wild type *C. utilis* uricase of SEQ ID NO: 1, whereas in certain other embodiments, one or more mutations may be non-conservative substitutions relative to wild type *C. utilis* uricase of SEQ ID NO: 1.

In another aspect, the invention provides a recombinant mutant *C. utilis* uricase enzyme comprising at least one (for example, one, two, three, four, or five) mutation(s) at a position corresponding to wild type *C. utilis* uricase of SEQ ID NO: 1, wherein the at least one mutation is present at a position selected from position 180, position 165, position 51, position 132, and position 44. In certain embodiments, one or more mutations may be conservative substitutions relative to wild type *C. utilis* uricase of SEQ ID NO: 1, whereas in certain other embodiments, one or more mutations may be non-conservative substitutions relative to wild type *C. utilis* uricase of SEQ ID NO: 1.

In another aspect, the invention provides a recombinant mutant *C. utilis* uricase comprising at least one (for example, one, two, three, four, or five) mutation(s) at a position corresponding to wild type *C. utilis* uricase of SEQ ID NO: 1, wherein the at least one mutation is present at a position selected from position 180, position 165, position 190, position 51, position 244, and position 132. In certain embodiments, one or more mutations may be conservative substitutions relative to wild type *C. utilis* uricase of SEQ ID NO: 1, whereas in certain other embodiments, one or more mutations may be non-conservative substitutions relative to wild type *C. utilis* uricase of SEQ ID NO: 1.

In certain embodiments, in any of the foregoing recombinant mutant *C. utilis* uricase enzymes, the uricase comprises two, three, four, five, six, seven, or eight mutations.

In certain embodiments, in any of the foregoing recombinant mutant *C. utilis* uricase enzymes, the uricase comprises the following substitutions (i) I180V, Y165F, E51K, I132R, and G44A, (ii) I180A, Y165F, E51K, I132R, and G44A, (iii) I180V, Y165F, V190G, E51K, I132R, and G44A, (iv) I180A, Y165F, V190G, E51K, I132R, and G44A, (v) I180V and Y165F, or (vi) I180V, Y165F, V190G, E51K, Q244K, and I132R, either alone or in combination with other substitutions.

In certain embodiments, the invention provides a recombinant mutant *C. utilis* uricase enzyme comprising three substitutions listed in a given row of TABLE 1 hereinbelow. In certain embodiments, the invention provides a recombinant mutant *C. utilis* uricase enzyme comprising five substitutions listed in a given row of TABLE 2 hereinbelow.

In another aspect, the invention provides a recombinant mutant *C. utilis* uricase having a half-life of at least 35 minutes in the presence of pancreatin, e.g., a half-life of 35-200 minutes in the presence of pancreatin, for example, under the conditions set forth in Example 1.

It is contemplated that any of the foregoing recombinant mutant *Candida utilis* uricases may, for example, have 5-50 fold, 10-40 fold, 10-30 fold, 20-40 fold, or 20-30 fold, higher stability in the presence of pancreatin, compared to the wild-type uricase. The uricase may, for example, be more stable at a pH less than about 6.5 compared to the template (or reference) wild-type uricase.

It is contemplated that any of the foregoing recombinant mutant *Candida utilis* uricases may, for example, be conjugated to a water soluble polymer, e.g., polyethylene glycol (PEG).

In certain embodiments, in any of the foregoing recombinant mutant *C. utilis* uricase enzymes, the uricase is isolated.

In another aspect, the invention provides an isolated nucleic acid comprising a nucleotide sequence encoding any one of the foregoing uricase enzymes. In certain embodiments, the nucleotide sequence is codon optimized for expression in a host cell, e.g., an *Escherichia coli* cell. The invention also provides an expression vector that comprises any one of the foregoing nucleotide sequences. Similarly, the invention provides host cells, e.g., *Escherichia coli* cells, comprising one or more of the foregoing expression vectors.

In another aspect, the invention provides a pharmaceutical composition comprising any one of the foregoing recombinant mutant *C. utilis* uricase enzymes and at least one pharmaceutically acceptable carrier and/or an excipient. The enzyme may be in a soluble form or in a crystal form. Furthermore, the composition may comprise a pH increasing agent. It is contemplated that the pharmaceutical composition may, for example, be formulated as an oral dosage form or a parenteral dosage form. In certain embodiments, the composition is a formulated as a powder, granulate, pellet, micropellet, or a minitablet. In certain embodiments, the composition is encapsulated in a capsule, e.g., a hydroxypropyl methylcellulose (HPMC) capsule, soft gelatin capsule, or a hard gelatin capsule, or the composition is formulated as a tablet dosage form.

In another aspect, the invention provides a method of treating a disease or disorder associated with an elevated amount of uric acid in a subject in need thereof. In certain embodiments, the disease or disorder is associated with an elevated amount of uric acid in plasma or urine of the subject. The method comprises administering to the subject an effective amount of any of the uricase enzymes or compositions described herein, to treat the disease or disorder in the subject.

In another aspect, the invention provides a method of treating hyperuricemia and/or hyperuricosuria in a subject in need thereof. The method comprises administering to the subject an effective amount of any of the uricase enzymes or compositions described herein, to treat the hyperuricemia and/or hyperuricosuria in the subject.

In another aspect, the invention provides a method of treating gout in a subject in need thereof. The method comprises administering to the subject an effective amount of any of the uricase enzymes or compositions described herein, to treat the gout in the subject.

In certain embodiments, in any of the foregoing methods, the recombinant mutant C. utilis uricase is administered in combination with a xanthine oxidase inhibitor (e.g., allopurinol or febuxostat), a uricosuric (e.g., probenecid, benzbromarone, losartan or lesinurad), or a combination thereof.

These and other aspects and features of the invention are described in the following detailed description and claims.

BRIEF DESCRIPTION OF THE DRAWINGS

The invention can be more completely understood with reference to the following drawings.

FIG. 1A is a SDS-PAGE gel depicting pancreatin, wild-type C. utilis uricase (His-UO), and wild-type C. utilis uricase following a 90 minute incubation with pancreatin.

FIG. 1B is a line graph depicting wild-type C. utilis uricase activity as measured by loss of substrate uric acid concentration following incubation of wild-type C. utilis uricase with pancreatin for the indicated time points. Uric acid concentration is measured by absorbance at 298 nm.

FIG. 2A is a line graph depicting the activity of the indicated mutant C. utilis uricases in the presence of pancreatin. Data from two independent preparations are depicted for each uricase. Activity values are normalized to the activity in presence of pancreatin at time zero. FIG. 2B is a line graph demonstrating the reproducibility across each preparation for the data depicted in FIG. 2A.

DETAILED DESCRIPTION

Figure 3:
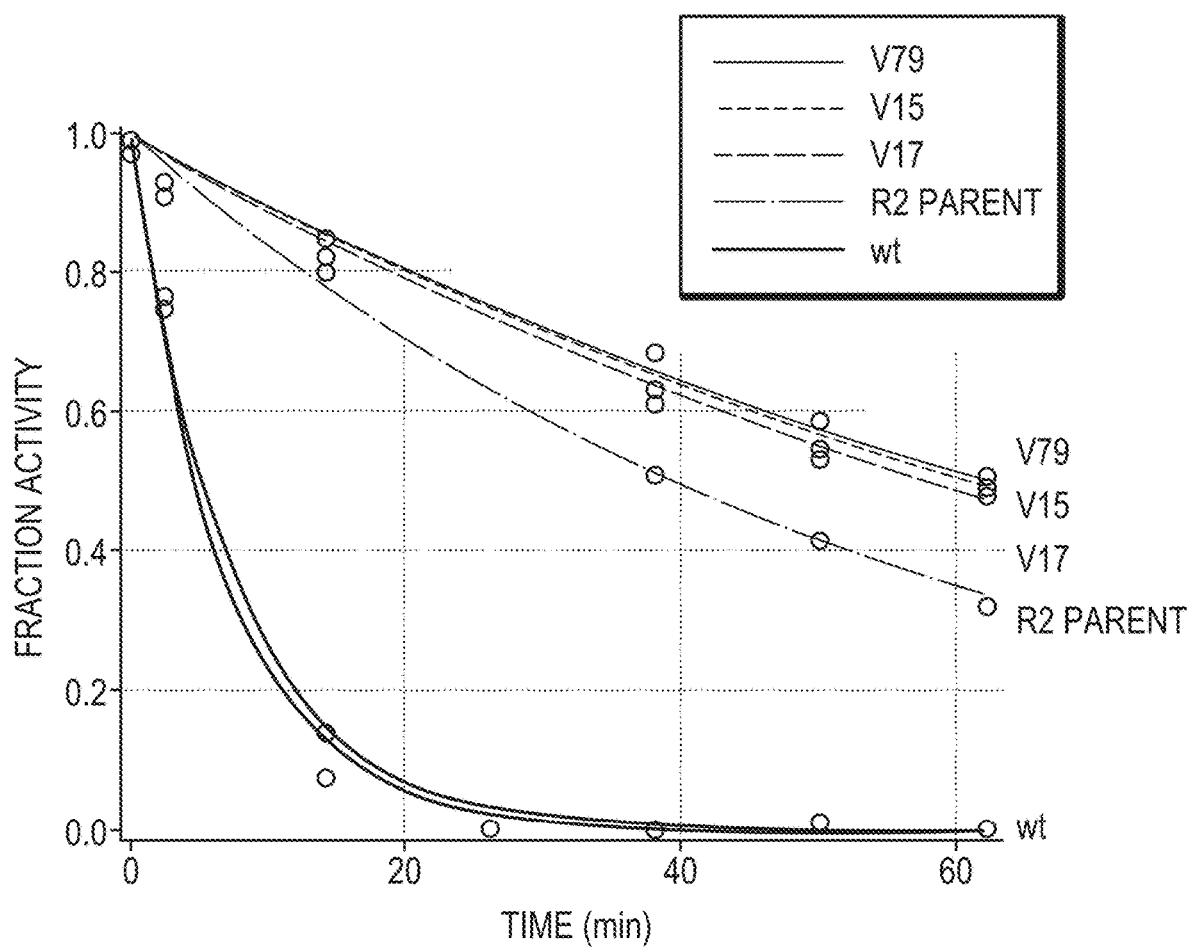
FIG. 3 is a line graph depicting the activity of the R2_V79, R2_15, R2_V16 and R2 Parent mutant C. utilis uricases following incubation with pancreatin for the indicated time-points. Activity values are normalized to the activity in presence of pancreatin at time zero.

The invention is based, in part, upon the discovery of recombinant uricase enzymes that are active in humans and have greater stability and/or activity than naturally occurring enzymes. In particular, the recombinant enzymes of the invention exhibit improved stability against proteolytic digestion by pancreatin (a collection of enzymes secreted by the pancreas) compared to naturally occurring versions of the enzyme. Furthermore, the recombinant enzymes of the invention may have greater specific activity than a wild type uricase enzyme. Furthermore, it is contemplated that the recombinant enzymes described herein, given their enhanced stability, may be suitable for oral administration, and therefore potentially safer and more tolerable than the commercially available, injectable forms of uricase (e.g., Krystexxa® and Elitek®), because it is contemplated that the enzymes will remain active within the intestines and will not be absorbed through the intestinal wall because the size of the recombinant enzyme would preclude passive absorption, and no receptor has been identified for active transport of the enzyme from the intestine.

Various features and aspects of the invention are discussed in more detail below.

I. Uric Acid and Uricase

Uric acid (also known as urate) is the final product of purine metabolism in humans and higher primates. Uricase (also known as urate oxidase or UrOx) degrades uric acid into allantoin by catalyzing the following reaction:

Uric acid+$O_2$+$H_2O$→5-hydroxyisourate+ $H_2O_2$→allantoin+$CO_2$.

Due to mutational silencing, humans and higher primates lack a functional uricase gene. However, functional uricase enzymes can be found in a wide range of organisms, including animals, plants, bacteria and fungi. One such organism is the yeast Candida utlilus (also known as Cyberlindnera jadinii or Torula yeast). C. utilis uricase is a homo-tetrameric enzyme that does not require a metal atom or an organic co-factor for catalysis. The amino acid sequence of wild type C. utilis uricase is as follows:

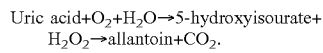

MSTTLSSSTYGKDNVKFLKVKKDPQNPKKQEVMEATVTCLLEGGFDTSYT

EADNSSIVPTDTVKNTILVLAKTTEIWPIERFAAKLATHFVEKYSHVSGV

SVKIVQDRWVKYAVDGKPHDHSFIHEGGEKRITDLYYKRSGDYKLSSAIK

DLTVLKSTGSMFYGYNKCDFTTLQPTTDRILSTDVDATWVWDNKKIGSVY

DIAKAADKGIFDNVYNQAREITLTTFALENSPSVQATMFNMATQILEKAC

SVYSVSYALPNKHYFLIDLKWKGLENDNELFYPSPHPNGLIKCTVVRKEK

TKL.

An exemplary nucleotide sequence encoding the wild type C. utilis uricase is as follows:

(SEQ ID NO: 7)
ATGTCGACGACCCTGAGCAGCAGCACCTATGGCAAAGATAATGTGAAATT

TCTGAAAGTCAAAAAAGACCCGCAGAACCCTAAGAAACAAGAGGTCATGG

-continued

```
AAGCGACCGTTACGTGTCTGCTGGAAGGCGGCTTCGACACCAGCTATACC

GAAGCGGATAATTCCTCCATCGTTCCGACCGATACGGTCAAGAACACCAT

TCTGGTTCTGGCCAAGACCACGGAAATCTGGCCAATTGAGCGCTTCGCCG

CGAAACTGGCGACCCATTTCGTTGAGAAGTACAGCCACGTGAGCGGCGTG

AGCGTTAAAATTGTTCAGGATCGTTGGGTCAAATATGCCGTGGATGGTAA

GCCGCATGACCACAGCTTTATTCACGAGGGTGGCGAGAAGCGTATCACTG

ACCTGTATTACAAGCGCAGCGGTGACTACAAATTGAGCAGCGCAATCAAA

GACCTGACGGTCCTGAAAAGCACCGGTTCTATGTTTTACGGTTACAATAA

GTGCGACTTTACGACGCTCCAACCGACTACGGACCGTATCCTGTCTACCG

ATGTAGACGCGACCTGGGTCTGGGATAACAAGAAAATTGGCAGCGTGTAC

GATATTGCGAAAGCCGCTGACAAGGGTATCTTCGACAACGTCTATAATCA

AGCGCGTGAGATCACCCTGACCACGTTTGCTCTGGAGAATTCCCCGAGCG

TTCAGGCGACCATGTTTAACATGGCAACGCAGATTTTGGAAAAGGCATGT

AGCGTGTACAGCGTGAGCTATGCATTGCCGAATAAGCACTACTTCCTGAT

TGATCTGAAGTGGAAGGGTCTGGAGAACGATAACGAACTGTTCTATCCGA

GCCCGCACCCGAATGGTCTGATCAAGTGCACCGTTGTGCGTAAAGAAAAG

ACTAAACTG.
```

II. Recombinant Mutant *Candida Utilis* Uricase Enzymes

Among other things, the invention provides a family of recombinant mutant *Candida Utilis* uricase enzymes that, for example, are useful in treating disorders associated with elevated levels of uric acid in a subject, for example, disorders associated with elevated levels of uric acid in plasma of the subject. In certain embodiments, the recombinant mutant *C. Utilis* uricase enzymes described herein have higher stability compared to the wild-type *C. Utilis* uricase, e.g., higher stability in the presence of pancreatin compared to the wild-type *C. Utilis* uricase, and are therefore better suited for oral delivery and activity in the intestines than wild-type *C. Utilis* uricase. Unless stated otherwise, as used herein, wild-type *C. Utilis* uricase refers a *C. Utilis* uricase having the amino acid sequence of SEQ ID NO: 1, or a functional fragment thereof that can catalyze the oxidation of uric acid to 5-hydroxyisourate. As used herein, the term "functional fragment" is understood to be a protein fragment of wild type *C. utilis* uricase of SEQ ID NO: 1 that has at least 50%, 60%, 70%, 80%, 90%, 95%, or 98% of the activity of wild type *C. utilis* uricase to catalyze the conversion of uric acid to 5-hydroxyisourate and/or allantoin.

In one aspect, the invention provides a recombinant mutant *Candida utilis* uricase enzyme that comprises at least one (for example, one, two, three, four, five, six, seven or eight) mutation(s) at a position corresponding to wild type *C. utilis* uricase of SEQ ID NO: 1, wherein the at least one mutation is selected from: (a) at position 180, isoleucine is substituted by valine or alanine (I180V or I180A), (b) at position 165, tyrosine is substituted by phenylalanine (Y165F), (c) at position 190, valine is substituted by glycine or alanine (V190G or V190A), (d) at position 51, glutamic acid is substituted by lysine (E51K), (e) at position 244, glutamine is substitute by lysine (Q244K), (f) at position 132, isoleucine is substituted by arginine or asparagine (I132R or I132N), (g) at position 97, valine is substituted by isoleucine (V97I), (h) at position 92, glutamic acid is substituted by asparagine (E92N), (i) at position 87, alanine is substituted by glycine (A87G), (j) at position 142, aspartic acid is substituted by glutamic acid (D142E), (k) at position 44, glycine is substituted by alanine (G44A), (l) at position 128, glycine is substituted by proline (G128P), (m) at position 236, alanine is substituted by asparagine (A236N), (n) at position 208, lysine is substituted by alanine (K208A), (o) at position 213, asparagine is substituted by alanine (N213A), (p) at position 140, serine is substituted by threonine (S140T), (q) at position 253, tyrosine is substituted by glutamine (Y253Q), (r) at position 84, alanine is substituted by serine (A84S), (s) at position 47, threonine is substituted by glutamic acid (T47E), (t) at position 95, serine is substituted by proline (S95P), (u) at position 103, lysine is substituted by threonine (K103T), (v) at position 134, aspartic acid is substituted by glutamic acid (D134E), (w) at position 136, tyrosine is substituted by arginine (Y136R), (x) at position 196, isoleucine is substituted by leucine (I196L), (y) at position 224, threonine is substituted by aspartic acid (T224D), (z) at position 285, proline is substituted by serine (P285S), and (aa) at position 296, valine is substituted by alanine (V296A).

In certain embodiments, the recombinant mutant *C. utilis* uricase enzyme comprises at least one mutation selected from: I180V, I180A, Y165F, V190G, V190A, E51K, Q244K, I132R, V97I, E92N, A87G, D142E, G44A, G128P, A236N, K208A, N213A, S140T, Y253Q, and A84S. In certain other embodiments, the uricase enzyme comprises at least one mutation selected from: I180V, I180A, Y165F, V190G, E51K, Q244K, I132R, V97I, E92N, A87G, D142E, and G44A. In certain other embodiments, the uricase enzyme comprises at least one mutation selected from: I180V, I180A, Y165F, V190G, E51K, I132R, and G44A. In certain other embodiments, the uricase enzyme comprises at least one mutation selected from: I180V, I180A, Y165F, E51K, I132R, and G44A. In certain other embodiments, the uricase enzyme comprises at least one mutation selected from: I180V, I180A, Y165F, V190G, E51K, Q244K, and I132R.

In another aspect, the invention provides a recombinant mutant *C. utilis* uricase enzyme comprising at least one (for example, one, two, three, four, five, or six) mutation(s) at a position corresponding to wild type *C. utilis* uricase of SEQ ID NO: 1, wherein the at least one mutation is present at a position selected from position 180, position 165, position 190, position 51, position 132, and position 44. In certain embodiments, one or more mutations may be conservative substitutions relative to wild type *C. utilis* uricase of SEQ ID NO: 1, whereas in certain other embodiments, one or more mutations may be non-conservative substitutions relative to wild type *C. utilis* uricase of SEQ ID NO: 1.

In another aspect, the invention provides a recombinant mutant *C. utilis* uricase enzyme comprising at least one (for example, one, two, three, four, or five) mutation(s) at a position corresponding to wild type *C. utilis* uricase of SEQ ID NO: 1, wherein the at least one mutation is present at a position selected from position 180, position 165, position 51, position 132, and position 44. In certain embodiments, one or more mutations may be conservative substitutions relative to wild type *C. utilis* uricase of SEQ ID NO: 1, whereas in certain other embodiments, one or more mutations may be non-conservative substitutions relative to wild type *C. utilis* uricase of SEQ ID NO: 1. As used herein, the term "conservative substitution" refers to a substitution with a structurally similar amino acid. For example, conservative substitutions may include those within the following groups: Ser and Cys; Leu, Ile, and Val; Glu and Asp; Lys and Arg;

Phe, Tyr, and Trp; and Gln, Asn, Glu, Asp, and His. Conservative substitutions may also be defined by the BLAST (Basic Local Alignment Search Tool) algorithm, the BLOSUM substitution matrix (e.g., BLOSUM 62 matrix), or the PAM substitution:p matrix (e.g., the PAM 250 matrix). Non conservative substitutions are amino acid substitutions that are not conservative substitutions.

In another aspect, the invention provides a recombinant mutant *C. utilis* uricase comprising at least one (for example, one, two, three, four, five, or six) mutation(s) at a position corresponding to wild type *C. utilis* uricase of SEQ ID NO: 1, wherein the at least one mutation is present at a position selected from position 180, position 165, position 190, position 51, position 244, and position 132. In certain embodiments, one or more mutations may be conservative substitutions relative to wild type *C. utilis* uricase of SEQ ID NO: 1, whereas in certain other embodiments, one or more mutations may be non-conservative substitutions relative to wild type *C. utilis* uricase of SEQ ID NO: 1.

In certain embodiments, in any of the foregoing recombinant mutant *C. utilis* uricase enzymes, the uricase comprises two, three, four, five, six, seven, or eight mutations.

In certain embodiments, in any of the foregoing recombinant mutant *C. utilis* uricase enzymes, the uricase comprises the following substitutions (i) I180V, Y165F, E51K, I132R, and G44A, (ii) I180A, Y165F, E51K, I132R, and G44A, (iii) I180V, Y165F, V190G, E51K, I132R, and G44A, (iv) I180A, Y165F, V190G, E51K, I132R, and G44A, (v) I180V and Y165F, or (vi) I180V, Y165F, V190G, E51K, Q244K, and I132R, either alone or in combination with other substitutions.

In one aspect, the invention provides a recombinant mutant *C. utilis* uricase enzyme comprising three substitutions listed in a given row of TABLE 1.

TABLE 1

| | | | |
|---|---|---|---|
| 1 | K130T | I180V | V190A |
| 2 | E51K | H125K | Q217L |
| 3 | Y165F | D201E | A242C |
| 4 | A83G | V97I | D201E |
| 5 | T38C | G128P | S251L |
| 6 | H125K | G128P | I196L |
| 7 | I180V | V214A | A242C |
| 8 | K130T | F170Y | A236N |
| 9 | Y165F | I180V | G197A |
| 10 | Y165F | Q217L | T243Q |
| 11 | A83G | H119S | Y165F |
| 12 | E51K | Y137A | Y165F |
| 13 | E92N | S95A | K130T |
| 14 | E92D | I180V | F281Y |
| 15 | G44A | V97I | S256N |
| 16 | S95A | V185I | Q217L |

In another aspect, the invention provides a recombinant mutant *C. utilis* uricase comprising five substitutions listed in a given row of TABLE 2.

TABLE 2

| | | | | | |
|---|---|---|---|---|---|
| 1 | Y165F | I180V | Q25A | T47E | S256D |
| 2 | Y165F | I180V | D142Q | Q217L | A236N |
| 3 | Y165F | I180V | G128P | R139E | D142E |
| 4 | Y165F | I180V | E51K | V97I | A236N |
| 5 | Y165F | I180V | D134E | R139E | V296A |
| 6 | Y165F | I180V | A87G | E220A | T224D |
| 7 | Y165F | I180V | G44A | G128P | K270E |
| 8 | Y165F | I180V | D142Q | I149L | F165Y |
| 9 | Y165F | I180V | G44A | Y136R | Y253Q |
| 10 | Y165F | I180V | E51K | I149L | D268N |
| 11 | Y165F | I180V | D142E | Q174G | S254N |

TABLE 2-continued

| | | | | | |
|---|---|---|---|---|---|
| 12 | Y165F | I180V | E92N | I149L | Y253Q |
| 13 | Y165F | I180V | I132N | V190A | N213A |
| 14 | Y165F | I180V | E51K | D142E | S256N |
| 15 | Y165F | I180V | G44A | E51K | I132R |
| 16 | Y165F | I180V | K103T | D134E | V180I |
| 17 | Y165F | I180V | A52S | A236N | S256N |
| 18 | Y165F | I180V | G128P | Y253Q | P285S |
| 19 | Y165F | I180V | E51K | P118I | S147T |
| 20 | Y165F | I180V | A84S | S140T | K204A |
| 21 | Y165F | I180V | E51K | G128P | F170Y |
| 22 | Y165F | I180V | E51K | A87G | D142Q |
| 23 | Y165F | I180V | E51K | G128P | N213A |
| 24 | Y165F | I180V | V97I | K103T | N213A |
| 25 | Y165F | I180V | K103T | F165Y | K208A |
| 26 | Y165F | I180V | Q25A | E51K | V296A |
| 27 | Y165F | I180V | K85I | P118I | E220A |
| 28 | Y165F | I180V | E51K | Y253Q | K270E |
| 29 | Y165F | I180V | Q25A | S95P | D142E |
| 30 | Y165F | I180V | V97I | G128P | S140T |
| 31 | Y165F | I180V | G128P | N193R | S254N |
| 32 | Y165F | I180V | S95P | I132N | Y253Q |
| 33 | Y165F | I180V | T47E | E92N | V97I |
| 34 | Y165F | I180V | E51K | D142E | Q217L |
| 35 | Y165F | I180V | A52S | K85I | Q244K |
| 36 | Y165F | I180V | A84S | G128P | S256N |
| 37 | Y165F | I180V | A84S | V97I | Y253Q |
| 38 | Y165F | I180V | A87G | I196L | S256N |
| 39 | Y165F | I180V | E51K | G128P | Y253Q |
| 40 | Y165F | I180V | D142E | I196L | K208A |
| 41 | Y165F | I180V | E51K | V97I | I196L |
| 42 | Y165F | I180V | Q174G | T224D | Y253Q |
| 43 | Y165F | I180V | I132R | D142E | V296A |
| 44 | Y165F | I180V | V97I | D142E | Y253Q |
| 45 | Y165F | I180V | A84S | D142E | V190A |
| 46 | Y165F | I180V | E92N | F170Y | N193R |
| 47 | Y165F | I180V | G128P | V180I | Q217L |
| 48 | Y165F | I180V | V97I | F170Y | S254N |
| 49 | Y165F | I180V | E92N | G128P | D142E |
| 50 | Y165F | I180V | A52S | I196L | S254N |
| 51 | Y165F | I180V | S140T | T224D | S256N |
| 52 | Y165F | I180V | S95P | K103T | G128P |
| 53 | Y165F | I180V | Y136R | Q244K | L274I |
| 54 | Y165F | I180V | A84S | Q217L | Q244K |
| 55 | Y165F | I180V | S95P | S140T | L274I |
| 56 | Y165F | I180V | D142E | N193R | L274I |
| 57 | Y165F | I180V | G44A | K204A | P285S |
| 58 | Y165F | I180V | V97I | D134E | Y137R |
| 59 | Y165F | I180V | A52S | E92N | S256D |
| 60 | Y165F | I180V | V97I | I132N | T224D |
| 61 | Y165F | I180V | F170Y | Q217L | D268N |
| 62 | Y165F | I180V | S95P | Q217L | S254N |
| 63 | Y165F | I180V | G44A | S95P | V97I |
| 64 | Y165F | I180V | D142E | S147T | F170Y |
| 65 | Y165F | I180V | S140T | F165Y | A236N |
| 66 | Y165F | I180V | V97I | K208A | D268N |
| 67 | Y165F | I180V | V97I | G128P | V190A |
| 68 | Y165F | I180V | Y136R | N193R | K270E |
| 69 | Y165F | I180V | Q25A | G128P | I149L |
| 70 | Y165F | I180V | V97I | P118I | D142E |
| 71 | Y165F | I180V | I132R | Q217L | P285S |
| 72 | Y165F | I180V | T47E | I196L | Y253Q |
| 73 | Y165F | I180V | E51K | Y136R | V190A |
| 74 | Y165F | I180V | E92N | V180I | D268N |
| 75 | Y165F | I180V | A87G | K204A | L274I |
| 76 | Y165F | I180V | V97I | S147T | K270E |
| 77 | Y165F | I180V | R139E | Q174G | Q244K |
| 78 | Y165F | I180V | A84S | A236N | V296A |
| 79 | Y165F | I180V | E51K | K85I | P285S |
| 80 | Y165F | I180V | V180I | Y253Q | S256D |
| 81 | Y165F | I180V | E51K | S140T | D142E |
| 82 | Y165F | I180V | V97I | E220A | S256N |
| 83 | Y165F | I180V | Q174G | N213A | P285S |
| 84 | Y165F | I180V | P118I | G128P | I196L |
| 85 | Y165F | I180V | D134E | K208A | Y253Q |

A recombinant mutant *Candida utilis* uricase disclosed herein may, for example, have higher specific activity than wild-type *C. utilis* uricase of SEQ ID NO.: 1. For example, a recombinant mutant *C. utilis* uricase may have from 5 to 50 fold higher specific activity than the wild-type *C. utilis* uricase. In certain embodiments, the uricase has from about 5 to about 50, from about 5 to about 40, from about 5 to about 30, from about 5 to about 20, from about 5 to about 10, from about 10 to about 50, from about 10 to about 40, from about 10 to about 30, from about 10 to about 20, from about 20 to about 50, from about 20 to about 40, from about 20 to about 30, from about 30 to about 50, from about 30 to about 40, from about 40 to about 50, about 5, about 10, about 20, about 30, about 40, or about 50 fold higher specific activity than wild-type *C. utilis* uricase.

Alternatively or in addition, the recombinant mutant *Candida utilis* uricase disclosed herein may, for example, have higher stability, e.g., higher stability in the presence of pancreatin, compared to the wild-type *C. utilis* uricase. For example, a recombinant mutant *C. utilis* uricase may have from 5 to 50 fold higher stability in the presence of pancreatin compared to the wild-type *C. utilis* uricase. In certain embodiments, the uricase has from about 5 to about 50, from about 5 to about 40, from about 5 to about 30, from about 5 to about 20, from about 5 to about 10, from about 10 to about 50, from about 10 to about 40, from about 10 to about 30, from about 10 to about 20, from about 20 to about 50, from about 20 to about 40, from about 20 to about 30, from about 30 to about 50, from about 30 to about 40, from about 40 to about 50, about 5, about 10, about 20, about 30, about 40, or about 50 fold higher stability in the presence of pancreatin compared to the wild-type *C. utilis* uricase.

Alternatively or in addition, the recombinant mutant *Candida utilis* uricase may, for example, have a half-life of at least 35 minutes in the presence of pancreatin. In certain embodiments, the uricase has a half-life of at least from about 35 to about 200 minutes, from about 35 to about 175 minutes, from about 35 to about 150 minutes, from about 35 to about 125 minutes, from about 35 to about 100 minutes, from about 35 to about 75 minutes, from about 35 to about 50 minutes, from about 50 to about 200 minutes, from about 50 to about 175 minutes, from about 50 to about 150 minutes, from about 50 to about 125 minutes, from about 50 to about 100 minutes, from about 50 to about 75 minutes, from about 75 to about 200 minutes, from about 75 to about 175 minutes, from about 75 to about 150 minutes, from about 75 to about 125 minutes, from about 75 to about 100 minutes, from about 100 to about 200 minutes, from about 100 to about 175 minutes, from about 100 to about 150 minutes, from about 100 to about 125 minutes, from about 125 to about 200 minutes, from about 125 to about 175 minutes, from about 125 to about 150 minutes, from about 150 to about 200 minutes, from about 150 to about 175 minutes, from about 175 to about 200 minutes, about 35 minutes, about 50 minutes, about 75 minutes, about 100 minutes, about 125 minutes, about 150 minutes, about 175 minutes, or about 200 minutes in the presence of pancreatin. Uricase stability or half-life may be measured by any method known in the art, including absorption based assays or SDS-PAGE as described in Example 1. Uricase half-life in the presence of pancreatin will depend upon the experimental conditions in which the half-life is measured, including, e.g., the concentration of pancreatin. In certain embodiments, the half-life of a disclosed recombinant mutant *Candida utilis* uricase in the presence of pancreatin is measured in the presence of 20 ng/µL or 80 ng/µL pancreatin, e.g., pancreatin available from Sigma-Aldrich (Cat No. P7545).

Alternatively or in addition, it is contemplated that a recombinant mutant *Candida utilis* uricase enzyme disclosed herein may, for example, have higher stability at a pH less than about 6.5 compared to the wild-type *C. utilis* uricase. For example, a recombinant mutant *C. utilis* uricase may have from 5 to 50 fold higher stability in the presence of pancreatin compared to the wild-type *C. utilis* uricase. In certain embodiments, the uricase enzyme has from about 5 to about 50, from about 5 to about 40, from about 5 to about 30, from about 5 to about 20, from about 5 to about 10, from about 10 to about 50, from about 10 to about 40, from about 10 to about 30, from about 10 to about 20, from about 20 to about 50, from about 20 to about 40, from about 20 to about 30, from about 30 to about 50, from about 30 to about 40, from about 40 to about 50, about 5, about 10, about 20, about 30, about 40, or about 50 fold higher stability at a pH less than about 6.5 compared to the wild-type *C. utilis* uricase. Uricase stability or half-life may be measured by any method known in the art, including absorption based assays or SDS-PAGE as described in Example 1.

The invention further provides a recombinant mutant *C. Utilis* uricase that comprises the following substitutions: Y165F, I180V, G44A, E51K, and I132R, e.g., a recombinant mutant *C. Utilis* uricase comprising the following amino acid sequence, e.g., a recombinant mutant uricase referred to as R2_V17 herein:

(SEQ ID NO: 2)
MSTTLSSSTYGKDNVKFLKVKKDPQNPKKQEVMEATVTCLLEGAFDTSYT

KADNSSIVPTDTVKNTILVLAKTTEIWPIERFAAKLATHFVEKYSHVSGV

SVKIVQDRWVKYAVDGKPHDHSFIHEGGEKRRTDLYYKRSGDYKLSSAIK

DLTVLKSTGSMFYGFNKCDFTTLQPTTDRVLSTDVDATWVWDNKKIGSVY

DIAKAADKGIFDNVYNQAREITLTTFALENSPSVQATMFNMATQILEKAC

SVYSVSYALPNKHYFLIDLKWKGLENDNELFYPSPHPNGLIKCTVVRKEK

TKL.

The invention further provides a recombinant mutant *C. Utilis* uricase that comprises the following substitutions: Y165F, I180V, E51K, V97I, and A236N, e.g., a recombinant mutant *C. Utilis* uricase comprising the following amino acid sequence, e.g., a recombinant mutant uricase referred to as R2_V4 herein:

(SEQ ID NO: 3)
MSTTLSSSTYGKDNVKFLKVKKDPQNPKKQEVMEATVTCLLEGGFDTSYT

KADNSSIVPTDTVKNTILVLAKTTEIWPIERFAAKLATHFVEKYSHISGV

SVKIVQDRWVKYAVDGKPHDHSFIHEGGEKRITDLYYKRSGDYKLSSAIK

DLTVLKSTGSMFYGFNKCDFTTLQPTTDRVLSTDVDATWVWDNKKIGSVY

DIAKAADKGIFDNVYNQAREITLTTFALENSPSVQNTMFNMATQILEKAC

SVYSVSYALPNKHYFLIDLKWKGLENDNELFYPSPHPNGLIKCTVVRKEK

TKL.

The invention further provides a recombinant mutant *C. Utilis* uricase that comprises the following substitutions: Y165F, I180V, I132R, Q217L, and P285S, e.g., a recombinant mutant *C. Utilis* uricase comprising the following amino acid sequence, e.g., a recombinant mutant uricase referred to as R2_V79 herein:

(SEQ ID NO: 4)
MSTTLSSSTYGKDNVKFLKVKKDPQNPKKQEVMEATVTCLLEGGFDTSYT

EADNSSIVPTDTVKNTILVLAKTTEIWPIERFAAKLATHFVEKYSHVSGV

SVKIVQDRWVKYAVDGKPHDHSFIHEGGEKRRTDLYYKRSGDYKLSSAIK

DLTVLKSTGSMFYGFNKCDFTTLQPTTDRVLSTDVDATWVWDNKKIGSVY

DIAKAADKGIFDNVYNLAREITLTTFALENSPSVQATMFNMATQILEKAC

SVYSVSYALPNKHYFLIDLKWKGLENDNELFYPSSHPNGLIKCTVVRKEK

TKL.

The invention further provides a recombinant mutant *C. Utilis* uricase that comprises the following substitutions: Y165F, I180V, E51K, V97I, and I196L, e.g., a recombinant mutant *C. Utilis* uricase comprising the following amino acid sequence, e.g., a recombinant mutant uricase referred to as R2_V47 herein:

(SEQ ID NO: 5)
MSTTLSSSTYGKDNVKFLKVKKDPQNPKKQEVMEATVTCLLEGGFDTSYT

KADNSSIVPTDTVKNTILVLAKTTEIWPIERFAAKLATHFVEKYSHISGV

SVKIVQDRWVKYAVDGKPHDHSFIHEGGEKRITDLYYKRSGDYKLSSAIK

DLTVLKSTGSMFYGFNKCDFTTLQPTTDRVLSTDVDATWVWDNKKLGSVY

DIAKAADKGIFDNVYNQAREITLTTFALENSPSVQATMFNMATQILEKAC

SVYSVSYALPNKHYFLIDLKWKGLENDNELFYPSPHPNGLIKCTVVRKEK

TKL.

The invention further provides a recombinant mutant *C. Utilis* uricase that comprises the following substitutions: Y165F, I180V, E51K, D142E, and Q217L, e.g., a recombinant mutant *C. Utilis* uricase comprising the following amino acid sequence, e.g., a recombinant mutant uricase referred to as R2_V39 herein:

(SEQ ID NO: 6)
MSTTLSSSTYGKDNVKFLKVKKDPQNPKKQEVMEATVICLLEGGFDTSYT

KADNSSIVPTDTVKNTILVLAKTTEIWPIERFAAKLATHFVEKYSHVSGV

SVKIVQDRWVKYAVDGKPHDHSFIHEGGEKRITDLYYKRSGEYKLSSAIK

DLTVLKSTGSMFYGFNKCDFTTLQPTTDRVLSTDVDATWVWDNKKIGSVY

DIAKAADKGIFDNVYNLAREITLTTFALENSPSVQATMFNMATQILEKAC

SVYSVSYALPNKHYFLIDLKWKGLENDNELFYPSPHPNGLIKCTVVRKEK

TKL.

The invention further provides a recombinant mutant *C. Utilis* uricase that has at least 90%, 95%, 96%, 97%, 98%, or 99% sequence identity to a *C. Utilis* uricase disclosed herein, and has at least 60% specific activity and/or 5 fold higher stability as wild type *C. Utilis* uricase. Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87:2264-2268; Altschul, (1993) J. MOL. EVOL. 36, 290-300; Altschul et al., (1997) NUCLEIC ACIDS RES. 25:3389-3402, incorporated by reference) are tailored for sequence similarity searching. For a discussion of basic issues in searching sequence databases, see Altschul et al., (1994) NATURE GENETICS 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; -r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

It is contemplated that a disclosed recombinant mutant *C. Utilis* uricase may be modified, engineered or chemically conjugated. For example, it is contemplated that a disclosed recombinant mutant *C. Utilis* uricase can be conjugated to an effector agent using standard in vitro conjugation chemistries. If the effector agent is a polypeptide, the uricase enzyme can be chemically conjugated to the effector or joined to the effector as a fusion protein. Construction of fusion proteins is within ordinary skill in the art.

In certain embodiments, depending upon a particular mode of administration or site of activity, a disclosed recombinant mutant *C. Utilis* uricase can be modified with a moiety that improves its stabilization and/or retention in circulation, e.g., in blood, serum, or other tissues. For example, a disclosed recombinant mutant *C. Utilis* uricase enzyme may be conjugated to a polymer, e.g., a substantially non-antigenic polymer, such as a polyalkylene oxide or a polyethylene oxide. In certain embodiments, a disclosed recombinant mutant *C. Utilis* uricase enzyme is conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof. Additional useful polymers include polyoxyalkylenes such as polyoxyethylene, polyoxypropylene, and block copolymers of polyoxyethylene and polyoxypropylene, polymethacrylates, carbomers, and branched or unbranched polysaccharides.

III. Uricase Production

Methods for producing uricase enzymes of the invention are known in the art. For example, DNA molecules encoding a uricase enzyme can be chemically synthesized using the sequence information provided herein. Synthetic DNA molecules can be ligated to other appropriate nucleotide sequences, including, e.g., expression control sequences, to produce conventional gene expression constructs encoding the desired uricase enzyme.

Nucleic acids encoding desired uricase enzymes can be incorporated (ligated) into expression vectors, which can be introduced into host cells through conventional transfection or transformation techniques. Transformed host cells can be grown under conditions that permit the host cells to express the genes that encode the uricase enzyme.

Nucleic acids encoding recombinant mutant *C. Utilis* uricases of the invention may be generated by mutating a nucleotide sequence encoding the wild type *C. utilis* uricase, e.g., SEQ ID NO: 7 disclosed herein, using methods known in the art. Furthermore, in certain embodiments, nucleic acids encoding recombinant mutant *C. Utilis* uricases of the invention may be codon optimized for expression in a heterologous cell, e.g., an *E. coli* cell, using methods known in the art.

In one embodiment, an exemplary nucleotide sequence encoding a recombinant mutant *C. Utilis* uricase that comprises the following substitutions: Y165F, I180V, G44A, E51K, and I132R, e.g., a recombinant mutant *C. Utilis* uricase referred to as R2_V17 herein, is as follows:

(SEQ ID NO: 8)
ATGTCGACGACCCTGAGCAGCAGCACCTATGGCAAAGATAATGTGAAATT

TCTGAAAGTCAAAAAAGACCCGCAGAACCCTAAGAAACAAGAGGTCATGG

AAGCGACCGTTACGTGTCTGCTGGAAGGCGCGTTCGACACCAGCTATACC

AAAGCGGATAATTCCTCCATCGTTCCGACCGATACGGTCAAGAACACCAT

TCTGGTTCTGGCCAAGACCACGGAAATCTGGCCAATTGAGCGCTTCGCCG

CGAAACTGGCGACCCATTTCGTTGAGAAGTACAGCCACGTGAGCGGCGTG

AGCGTTAAAATTGTTCAGGATCGTTGGGTCAAATATGCCGTGGATGGTAA

GCCGCATGACCACAGCTTTATTCACGAGGGTGGCGAGAAGCGTCGTACTG

ACCTGTATTACAAGCGCAGCGGTGACTACAAATTGAGCAGCGCAATCAAA

GACCTGACGGTCCTGAAAAGCACCGGTTCTATGTTTTACGGTTTCAATAA

GTGCGACTTTACGACGCTCCAACCGACTACGGACCGTGTTCTGTCTACCG

ATGTAGACGCGACCTGGGTCTGGGATAACAAGAAAATTGGCAGCGTGTAC

GATATTGCGAAAGCCGCTGACAAGGGTATCTTCGACAACGTCTATAATCA

AGCGCGTGAGATCACCCTGACCACGTTTGCTCTGGAGAATTCCCCGAGCG

TTCAGGCGACCATGTTTAACATGGCAACGCAGATTTTGGAAAAGGCATGT

AGCGTGTACAGCGTGAGCTATGCATTGCCGAATAAGCACTACTTCCTGAT

TGATCTGAAGTGGAAGGGTCTGGAGAACGATAACGAACTGTTCTATCCGA

GCCCGCACCCGAATGGTCTGATCAAGTGCACCGTTGTGCGTAAAGAAAAG

ACTAAACTG.

An exemplary nucleotide sequence encoding a recombinant mutant *C. Utilis* uricase that comprises the following substitutions: Y165F, I180V, E51K, V97I, and A236N, e.g., a recombinant mutant *C. Utilis* uricase referred to as R2_V4 herein, is as follows:

(SEQ ID NO: 9)
ATGTCGACGACCCTGAGCAGCAGCACCTATGGCAAAGATAATGTGAAATT

TCTGAAAGTCAAAAAAGACCCGCAGAACCCTAAGAAACAAGAGGTCATGG

AAGCGACCGTTACGTGTCTGCTGGAAGGCGGCTTCGACACCAGCTATACC

AAAGCGGATAATTCCTCCATCGTTCCGACCGATACGGTCAAGAACACCAT

TCTGGTTCTGGCCAAGACCACGGAAATCTGGCCAATTGAGCGCTTCGCCG

CGAAACTGGCGACCCATTTCGTTGAGAAGTACAGCCACATCAGCGGCGTG

AGCGTTAAAATTGTTCAGGATCGTTGGGTCAAATATGCCGTGGATGGTAA

GCCGCATGACCACAGCTTTATTCACGAGGGTGGCGAGAAGCGTATCACTG

ACCTGTATTACAAGCGCAGCGGTGACTACAAATTGAGCAGCGCAATCAAA

GACCTGACGGTCCTGAAAAGCACCGGTTCTATGTTTTACGGTTTCAATAA

GTGCGACTTTACGACGCTCCAACCGACTACGGACCGTGTTCTGTCTACCG

ATGTAGACGCGACCTGGGTCTGGGATAACAAGAAAATTGGCAGCGTGTAC

GATATTGCGAAAGCCGCTGACAAGGGTATCTTCGACAACGTCTATAATCA

AGCGCGTGAGATCACCCTGACCACGTTTGCTCTGGAGAATTCCCCGAGCG

TTCAGAACACCATGTTTAACATGGCAACGCAGATTTTGGAAAAGGCATGT

AGCGTGTACAGCGTGAGCTATGCATTGCCGAATAAGCACTACTTCCTGAT

TGATCTGAAGTGGAAGGGTCTGGAGAACGATAACGAACTGTTCTATCCGA

GCCCGCACCCGAATGGTCTGATCAAGTGCACCGTTGTGCGTAAAGAAAAG

ACTAAACTG.

An exemplary nucleotide sequence encoding a recombinant mutant *C. Utilis* uricase that comprises the following substitutions: Y165F, I180V, I132R, Q217L, and P285S, e.g., a recombinant mutant *C. Utilis* uricase referred to as R2_V79 herein, is as follows:

(SEQ ID NO: 10)
ATGTCGACGACCCTGAGCAGCAGCACCTATGGCAAAGATAATGTGAAATT

TCTGAAAGTCAAAAAAGACCCGCAGAACCCTAAGAAACAAGAGGTCATGG

AAGCGACCGTTACGTGTCTGCTGGAAGGCGGCTTCGACACCAGCTATACC

GAAGCGGATAATTCCTCCATCGTTCCGACCGATACGGTCAAGAACACCAT

TCTGGTTCTGGCCAAGACCACGGAAATCTGGCCAATTGAGCGCTTCGCCG

CGAAACTGGCGACCCATTTCGTTGAGAAGTACAGCCACGTGAGCGGCGTG

AGCGTTAAAATTGTTCAGGATCGTTGGGTCAAATATGCCGTGGATGGTAA

GCCGCATGACCACAGCTTTATTCACGAGGGTGGCGAGAAGCGTCGTACTG

ACCTGTATTACAAGCGCAGCGGTGACTACAAATTGAGCAGCGCAATCAAA

GACCTGACGGTCCTGAAAAGCACCGGTTCTATGTTTTACGGTTTCAATAA

An exemplary nucleotide sequence encoding a recombinant mutant *C. Utilis* uricase that comprises the following substitutions: Y165F, I180V, E51K, V97I, and I196L, e.g., a recombinant mutant *C. Utilis* uricase referred to as R2_V47 herein, is as follows:

(SEQ ID NO: 11)
```
ATGTCGACGACCCTGAGCAGCAGCACCTATGGCAAAGATAATGTGAAATT
TCTGAAAGTCAAAAAAGACCCGCAGAACCCTAAGAAACAAGAGGTCATGG
AAGCGACCGTTACGTGTCTGCTGGAAGGCGGCTTCGACACCAGCTATACC
AAAGCGGATAATTCCTCCATCGTTCCGACCGATACGGTCAAGAACACCAT
TCTGGTTCTGGCCAAGACCACGGAAATCTGGCCAATTGAGCGCTTCGCCG
CGAAACTGGCGACCCATTTCGTTGAGAAGTACAGCCACATCAGCGGCGTG
AGCGTTAAAATTGTTCAGGATCGTTGGGTCAAATATGCCGTGGATGGTAA
GCCGCATGACCACAGCTTTATTCACGAGGGTGGCGAGAAGCGTATCACTG
ACCTGTATTACAAGCGCAGCGGTGACTACAAATTGAGCAGCGCAATCAAA
GACCTGACGGTCCTGAAAAGCACCGGTTCTATGTTTTACGGTTTCAATAA
GTGCGACTTTACGACGCTCCAACCGACTACGGACCGTGTTCTGTCTACCG
ATGTAGACGCGACCTGGGTCTGGGATAACAAGAAACTGGGCAGCGTGTAC
GATATTGCGAAAGCCGCTGACAAGGGTATCTTCGACAACGTCTATAATCA
AGCGCGTGAGATCACCCTGACCACGTTTGCTCTGGAGAATTCCCCGAGCG
TTCAGGCGACCATGTTTAACATGGCAACGCAGATTTTGGAAAAGGCATGT
AGCGTGTACAGCGTGAGCTATGCATTGCCGAATAAGCACTACTTCCTGAT
TGATCTGAAGTGGAAGGGTCTGGAGAACGATAACGAACTGTTCTATCCGA
GCCCGCACCCGAATGGTCTGATCAAGTGCACCGTTGTGCGTAAAGAAAAG
ACTAAACTG.
```

An exemplary nucleotide sequence encoding a recombinant mutant *C. Utilis* uricase that comprises the following substitutions: Y165F, I180V, E51K, D142E, and Q217L, e.g., a recombinant mutant *C. Utilis* uricase referred to as R2_V39 herein, is as follows:

(SEQ ID NO: 12)
```
ATGTCGACGACCCTGAGCAGCAGCACCTATGGCAAAGATAATGTGAAATT
TCTGAAAGTCAAAAAAGACCCGCAGAACCCTAAGAAACAAGAGGTCATGG
AAGCGACCGTTACGTGTCTGCTGGAAGGCGGCTTCGACACCAGCTATACC
AAAGCGGATAATTCCTCCATCGTTCCGACCGATACGGTCAAGAACACCAT
TCTGGTTCTGGCCAAGACCACGGAAATCTGGCCAATTGAGCGCTTCGCCG
CGAAACTGGCGACCCATTTCGTTGAGAAGTACAGCCACGTGAGCGGCGTG
AGCGTTAAAATTGTTCAGGATCGTTGGGTCAAATATGCCGTGGATGGTAA
GCCGCATGACCACAGCTTTATTCACGAGGGTGGCGAGAAGCGTATCACTG
ACCTGTATTACAAGCGCAGCGGTGAGTACAAATTGAGCAGCGCAATCAAA
GACCTGACGGTCCTGAAAAGCACCGGTTCTATGTTTTACGGTTTCAATAA
GTGCGACTTTACGACGCTCCAACCGACTACGGACCGTGTTCTGTCTACCG
ATGTAGACGCGACCTGGGTCTGGGATAACAAGAAAATTGGCAGCGTGTAC
GATATTGCGAAAGCCGCTGACAAGGGTATCTTCGACAACGTCTATAATCT
GGCGCGTGAGATCACCCTGACCACGTTTGCTCTGGAGAATTCCCCGAGCG
TTCAGGCGACCATGTTTAACATGGCAACGCAGATTTTGGAAAAGGCATGT
AGCGTGTACAGCGTGAGCTATGCATTGCCGAATAAGCACTACTTCCTGAT
TGATCTGAAGTGGAAGGGTCTGGAGAACGATAACGAACTGTTCTATCCGA
GCCCGCACCCGAATGGTCTGATCAAGTGCACCGTTGTGCGTAAAGAAAAG
ACTAAACTG.
```

Specific expression and purification conditions will vary depending upon the expression system employed. For example, if a gene is to be expressed in *E. coli*, it can be cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

A uricase enzyme can be produced by growing (culturing) a host cell transfected with an expression vector encoding such uricase enzyme, under conditions that permit expression of the uricase enzyme. Following expression, the uricase enzyme can be harvested and purified or isolated using techniques known in the art, e.g., affinity tags such as glutathione-S-transferase (GST) and histidine tags. An exemplary expression and purification protocol for a uricase enzyme is described in Liu et al. (2011) APPL. MICROBIOL. BIOTECHNOL. 92(3):529-37.

IV. Pharmaceutical Compositions

For therapeutic use, a recombinant uricase enzyme described herein preferably is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. [1975]. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, the uricase enzymes can be formulated, or co-administered (either at the same time or sequentially), for example, by an enteral route (e.g., orally), with a pH increasing agent, for example, a protein pump inhibitor (PPI), to enhance the stability of the uricase enzyme, for example, in an acidic environment, for example, in the gastrointestinal tract.

Proton pump inhibitors are a group of drugs whose main action is pronounced and long-lasting reduction of gastric acid production. Proton pump inhibitors act by blocking the hydrogen/potassium adenosine triphosphatase enzyme system (the $H^+/K^+$ ATPase, or more commonly just gastric proton pump) of the gastric parietal cell. The proton pump is the terminal stage in gastric acid secretion, being directly responsible for secreting Et ions into the gastric lumen, making it an ideal target for inhibiting acid secretion. Examples of proton pump inhibitors include: Omeprazole (brand names: LOSEC®, PRILOSEC®, ZEGERID®); Lansoprazole (brand names: PREVACID®, ZOTON®, INHIBITOL®); Esomeprazole (brand names: NEXIUM®); and Pantoprazole (brand names: PROTONIX®, SOMAC®, PANTOLOC®).

Pharmaceutical compositions containing a recombinant uricase enzyme disclosed herein can be presented in a dosage unit form and can be prepared by any suitable method. A pharmaceutical composition should be formulated to be compatible with its intended route of administration. The pharmaceutical compositions may be in a variety of forms. These include, for example, liquid, semi-solid and solid dosage forms, such as liquid solutions, dispersions or suspensions, tablets, pills, powders, liposomes and suppositories. The preferred form will depend upon the intended mode of administration and therapeutic application.

Although the compositions preferably are formulated for administration enterally (for example, orally), such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and infrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Depending upon the mode of administration, for example, by parenteral administration, it may be desirable to produce a pharmaceutical formulation that is sterile. Sterilization can be accomplished by any suitable method, e.g., filtration through sterile filtration membranes. Where the composition is lyophilized, filter sterilization can be conducted prior to or following lyophilization and reconstitution.

In certain embodiments, a disclosed composition comprises a polyionic reagent which may, e.g., coat the uricase (e.g., the composition comprises a polyionic coating). Exemplary polyionic reagents include PSS (poly(Sodium 4-styrenesulfonate), PAA (poly Acrylic acid sodium salt), PMG (poly(methylene-co-guanidine) hydrochloride), DS (dextran sulfate), PMA (poly(methyl acrylate)), or PVS (polyvinylsiloxane).

V. Therapeutic Uses

The recombinant uricase enzymes disclosed herein can be used to treat various diseases or disorders associated with an elevated amount of uric acid in a subject. As used herein, "elevated amount of uric acid in a subject" may refer to an elevated amount of uric acid in a body fluid (e.g., blood, plasma, serum, or urine), tissue and/or cell in a subject, relative to a subject without the disease or disorder. In human blood, uric acid concentrations between 2.4-6 mg/dL for females and 3.4-7.2 mg/dL for males are considered normal by the Clinical Mayo Reference laboratory.

The invention provides a method of treating a disease or disorder associated with an elevated amount of uric acid in a subject. In certain embodiments, the disease or disorder is associated with an elevated amount of uric acid in plasma of the subject. The method comprises administering to the subject an effective amount of a disclosed recombinant uricase, either alone or in a combination with another therapeutic agent to treat the disease or disorder in the subject. The term "effective amount" as used herein refers to the amount of an active agent (e.g., a recombinant uricase of the present invention) sufficient to effect beneficial or desired results. An effective amount can be administered in one or more administrations, applications or dosages and is not intended to be limited to a particular formulation or administration route.

In certain embodiments, the method comprises orally administering to the subject an effective amount of a disclosed recombinant uricase, either alone or in a combination with another therapeutic agent to treat the disease or disorder in the subject. It is contemplated that, in certain embodiments, the orally administered recombinant uricase may avoid passive absorption in the intestine due to its size, and if metabolized, the novel recombinant uricase of the present invention orally administered with food would be metabolized in a manner similar to that of any other ingested protein.

As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

Examples of diseases or disorders associated with an elevated amount of uric acid include a metabolic disorder, e.g., metabolic syndrome, hyperuricemia, gout (e.g., gouty arthritis), Lesch-Nyhan syndrome, cardiovascular disease, diabetes, hypertension, renal disease, metabolic syndrome, uric acid nephrolithiasis (or kidney stones (see Wiederkehr et al. (2011), *Clin. Rev. Bone. Miner. Metab.,* 9(3-4):207-217 ("Uric acid nephrolithiasis is characteristically a manifestation of a systemic metabolic disorder. It has a prevalence of about 10% among all stone formers, the third most common type of kidney stone in the industrialized world.))), tumor lysis syndrome, and hyperuricosuria.

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In certain embodiments, a method or composition described herein, is administered in combination with one or more additional therapies selected from a xanthine-oxidase inhibitor (e.g., allopurinol, TEI-6720 (2-(3-cyano-4-isobutoxyphenyl)-4-methyl-5-thiazolecarboxylic acid), febuxostat (2-[3-cyano-4-isobutoxyphenyl]-4-methylthiazole-5-carboxylic acid), oxypurinol, or pteridylaldehyde), a uricosuric (e.g., probenecid, lesinurad, sulfinpyrazone, sulfinpyrazone, or fenofibrate), ethylenediaminetetraacetic acid, acetazolamide, a potassium supplement, and any combination thereof.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1—Recombinant Mutant *Candida utilis* Uricase Design and Testing

This example describes the design and testing of recombinant mutant *Candida utilis* uricases with improved pancreatin stability.

95 mutant *C. utilis* uricases were designed each with three amino acid substitutions relative to the wild-type sequence. The mutant *C. utilis* uricases are indicated as R1_V1-R1_V95.

Briefly, DNA fragments encoding the 95 mutant *C. utilis* uricases were cloned into a rhamanose pD861-NH expression vector (ATUM, Newark, Calif.) that encodes a N-terminal His-tag. All constructs were confirmed by sequencing. Following expression in *Escherichia coli* cells, each recombinant mutant *C. utilis* uricase enzyme was bound to a Ni-NTA column and eluted in a buffer containing 25 mM Tris-HCl pH 8.0, 100 mM NaCl, 200 mM imidazole, and 50% (v/v) glycerol.

The purified recombinant mutant *C. utilis* uricases were tested for enzymatic activity in the presence of pancreatin (Sigma-Aldrich Cat No. P7545; which converts at least 25 times its weight of potato starch into soluble carbohydrates in 5 minutes in water at 40° C., digests at least 25 times its weight of casein in 60 minutes at pH 7.5 at 40° C., and releases at least 2 microequivalents of acid per minute per mg pancreatin from olive oil at pH 9.0 at 37° C.) to determine pancreatin stability. Briefly, 25 ng/μL of uricase was incubated with 20 ng/μL of pancreatin at 37° C. for up to 200 minutes. The assay was performed in simulated intestinal fluid (SIF) buffer (50 mM potassium phosphate, pH 6.8) in 96 well plates. Following incubation with pancreatin for the indicated time points, enzymatic activity was monitored using an absorption based assay. Uric acid has a strong absorbance at 293 nm, and the enzymatic oxidation of uric acid to 5-hydroxyisourate by uricase results in a corresponding drop in 293 nm absorbance over time.

Results for *C. utilis* uricase mutants with the most improved pancreatin stability were confirmed over multiple protein preparations. Representative data for wild type *C. utilis* uricase is depicted in FIG. 1, and representative data for a subset of mutant *C. utilis* uricases is depicted in FIG. 2.

TABLE 3 depicts the amino acid substitutions for the 95 recombinant mutant *C. utilis* uricases, as well as the specific activity (04/minute per 1.2 ng/μl of uricase), pancreatin stability (half-life, minutes) and expression yield (μg/ml) for each enzyme. "nd" indicates that activity and stability measurements were not determined due to insufficient expression yield.

TABLE 3

| Clone | Specific Activity* | Pancreatin Stability# | Expression (μg/ml) | Substitutions | | |
|---|---|---|---|---|---|---|
| WT | 4-4.9 | 10-19 | 200-299 | | | |
| R1_V1 | >5 | 0-9 | >300 | G44A | S95P | P285S |
| R1_V2 | 4-4.9 | 0-9 | 200-299 | S140T | Y163H | S254N |
| R1_V3 | 3-3.9 | 0-9 | 200-299 | T38C | H119S | T243Q |
| R1_V4 | 4-4.9 | 0-9 | 100-199 | E92D | Y137A | K167R |
| R1_V5 | >5 | >50 | 10-99 | K130T | I180V | V190A |
| R1_V6 | 4-4.9 | 0-9 | 200-299 | Y136H | I196L | K208G |
| R1_V7 | 4-4.9 | 10-19 | 200-299 | V97I | Y185I | |
| R1_V8 | 4-4.9 | 0-9 | 200-299 | T62S | I196L | D201E |
| R1_V9 | 4-4.9 | 0-9 | 200-299 | V69I | Q244D | H286C |
| R1_V10 | 0-2.9 | 0-9 | 200-299 | H125K | Y163H | Y253Q |
| R1_V11 | 0-2.9 | 0-9 | 100-199 | A84S | H125K | N276D |
| R1_V12 | 3-3.9 | 0-9 | 100-199 | H119S | Y136D | S254N |
| R1_V13 | >5 | 0-9 | >300 | K130T | D142E | F239Y |
| R1_V14 | 4-4.9 | 0-9 | 100-199 | K167R | T243Q | S254N |
| R1_V15 | 0-2.9 | 0-9 | 10-99 | Y136H | Y143A | M161Q |
| R1_V16 | 3-3.9 | 20-49 | 200-299 | E51K | H125K | Q217L |
| R1_V17 | >5 | 0-9 | >300 | D142E | Y163H | D201E |
| R1_V18 | 4-4.9 | 0-9 | 200-299 | G44A | E51K | G159N |
| R1_V19 | 4-4.9 | 0-9 | 200-299 | Y136D | I196L | S251L |
| R1_V20 | 4-4.9 | 20-49 | 200-299 | Y165F | D201E | A242C |
| R1_V21 | >5 | 10-19 | 10-99 | A83G | V97I | D201E |
| R1_V22 | 4-4.9 | 10-19 | 200-299 | E92N | Q244D | Y253Q |
| R1_V23 | 4-4.9 | 0-9 | 200-299 | D46E | V97I | H286C |
| R1_V24 | 3-3.9 | 0-9 | 200-299 | D46E | V69I | G159N |
| R1_V25 | 4-4.9 | 0-9 | 200-299 | F170Y | S198G | V214A |
| R1_V26 | 4-4.9 | 0-9 | 200-299 | S95A | A113E | H286C |
| R1_V27 | 4-4.9 | 0-9 | 100-199 | E92D | Y136D | H286A |
| R1_V28 | 0-2.9 | 0-9 | 200-299 | Y136D | Y163H | N276D |
| R1_V29 | nd | nd | 0-9 | Y143A | S251L | H286C |
| R1_V30 | nd | nd | 0-9 | A83G | Y163H | G197A |
| R1_V31 | >5 | 10-19 | 200-299 | T38C | G128P | S251L |
| R1_V32 | 3-3.9 | 10-19 | 200-299 | H125K | G128P | I196L |
| R1_V33 | 4-4.9 | 0-9 | 10-99 | L70E | V190A | A236N |
| R1_V34 | 4-4.9 | 10-19 | 100-199 | A242C | Q244D | P285S |
| R1_V35 | 3-3.9 | 0-9 | 100-199 | E92N | D201E | E229D |
| R1_V36 | 4-4.9 | 0-9 | 200-299 | Y136H | S256N | F281Y |
| R1_V37 | 4-4.9 | 0-9 | 10-99 | L70E | V105I | Q217L |
| R1_V38 | 4-4.9 | 20-49 | 200-299 | I180V | V214A | A242C |
| R1_V39 | nd | nd | 0-9 | V105I | Y143A | A236N |
| R1_V40 | 4-4.9 | 10-19 | 200-299 | K130T | F170Y | A236N |
| R1_V41 | nd | nd | 0-9 | G44A | S140T | Y143A |
| R1_V42 | 4-4.9 | 10-19 | 200-299 | V105I | S140T | D142E |
| R1_V43 | 4-4.9 | 10-19 | 10-99 | A83G | A84S | V185I |
| R1_V44 | 4-4.9 | 10-19 | 100-199 | A113E | K208G | Q244D |
| R1_V45 | 3-3.9 | 0-9 | 200-299 | V69I | F239Y | S251L |
| R1_V46 | 3-3.9 | 0-9 | 100-199 | D46E | T62S | A242C |
| R1_V47 | 4-4.9 | 0-9 | >300 | S95P | F281Y | H286A |
| R1_V48 | 3-3.9 | 0-9 | 200-299 | T62S | Q244D | F281Y |
| R1_V49 | 4-4.9 | 0-9 | 200-299 | A113E | Y253Q | S256N |
| R1_V50 | 4-4.9 | 0-9 | 200-299 | V105I | G128P | E229D |
| R1_V51 | 4-4.9 | 10-19 | 200-299 | A84S | S140T | F281Y |
| R1_V52 | >5 | 0-9 | 100-199 | G197A | Y253Q | H286A |
| R1_V53 | 4-4.9 | 10-19 | 200-299 | G44A | G128P | V185I |
| R1_V54 | 4-4.9 | 0-9 | 10-99 | V97I | G197A | V214A |
| R1_V55 | 0-2.9 | 0-9 | 200-299 | T62S | H119S | M161Q |
| R1_V56 | 4-4.9 | 0-9 | 200-299 | V69I | A84S | A236N |
| R1_V57 | >5 | >50 | 10-99 | Y165F | I180V | G197A |
| R1_V58 | 4-4.9 | 20-49 | 200-299 | Y165F | Q217L | T243Q |
| R1_V59 | 3-3.9 | 0-9 | 200-299 | G159N | K167R | F239Y |
| R1_V60 | 4-4.9 | 10-19 | 200-299 | E92D | S140T | P285S |
| R1_V61 | 4-4.9 | 0-9 | 10-99 | V69I | L70E | E92N |
| R1_V62 | 4-4.9 | 0-9 | 10-99 | L70E | K130T | T243Q |
| R1_V63 | 3-3.9 | 0-9 | 200-299 | H119S | K208G | H286A |
| R1_V64 | 0-2.9 | 20-49 | 100-199 | A83G | H119S | Y165F |
| R1_V65 | 4-4.9 | 10-19 | 100-199 | T38C | M161Q | S254N |
| R1_V66 | 4-4.9 | 0-9 | 200-299 | S95P | Q217L | A236N |
| R1_V67 | 4-4.9 | 20-49 | 100-199 | E51K | Y137A | Y165F |
| R1_V68 | 4-4.9 | 10-19 | 100-199 | E92N | S95A | K130T |
| R1_V69 | 4-4.9 | 0-9 | 200-299 | A84S | G159N | S198G |
| R1_V70 | 4-4.9 | 20-49 | 200-299 | E92D | I180V | F281Y |
| R1_V71 | 0-2.9 | 0-9 | 100-199 | G159N | F170Y | N276D |
| R1_V72 | 4-4.9 | 20-49 | 200-299 | G44A | V97I | S256N |
| R1_V73 | 4-4.9 | 10-19 | 10-99 | E92D | V190A | S198G |
| R1_V74 | 4-4.9 | 0-9 | 200-299 | S95A | F239Y | S256N |
| R1_V75 | 4-4.9 | 0-9 | 200-299 | K208G | V214A | H286C |
| R1_V76 | 4-4.9 | 0-9 | 200-299 | T38C | D142E | E229D |
| R1_V77 | 0-2.9 | 0-9 | 100-199 | H125K | Y136H | V214A |
| R1_V78 | 4-4.9 | 0-9 | 200-299 | S95P | Y137A | D142E |
| R1_V79 | 4-4.9 | 10-19 | 200-299 | S95A | V185I | Q217L |
| R1_V80 | 4-4.9 | 10-19 | 200-299 | E51K | F170Y | T243Q |
| R1_V81 | nd | nd | 0-9 | T38C | Y136D | Y143A |
| R1_V82 | 4-4.9 | 10-19 | 200-299 | M161Q | S198G | A242C |
| R1_V83 | 4-4.9 | 0-9 | 200-299 | S95P | V105I | S256N |
| R1_V84 | nd | nd | 0-9 | L70E | Y137A | F170Y |
| R1_V85 | 4-4.9 | 0-9 | 100-199 | D46E | V190A | E229D |
| R1_V86 | 4-4.9 | 0-9 | 200-299 | S95A | K167R | P285S |
| R1_V87 | 4-4.9 | 0-9 | 200-299 | V190A | F239Y | H286A |
| R1_V88 | 3-3.9 | 0-9 | 100-199 | T62S | E92N | Y137A |
| R1_V89 | 4-4.9 | 0-9 | 200-299 | D46E | A113E | G128P |
| R1_V90 | >5 | 10-19 | 200-299 | I196L | Y253Q | P285S |
| R1_V91 | 4-4.9 | 0-9 | 200-299 | E51K | M161Q | V185I |
| R1_V92 | 0-2.9 | 0-9 | 10-99 | A83G | A113E | N276D |

TABLE 3-continued

| Clone | Specific Activity* | Pancreatin Stability# | Expression (µg/ml) | Substitutions | | |
|---|---|---|---|---|---|---|
| R1_V93 | 4-4.9 | 0-9 | 10-99 | G197A | K208G | S251L |
| R1_V94 | 4-4.9 | 0-9 | 200-299 | K167R | I180V | E229D |
| R1_V95 | 0-2.9 | 0-9 | 10-99 | S198G | S254N | N276D |

*Specific Activity unit: µM/minute per 1.2 ng/µl of uricase; #Pancreatin Stability unit: half-life, minutes An analysis of the 95 recombinant mutant *C. utilis* uricases using protein modeling tools identified Y165F and I180V as key substitutions contributing towards improved pancreatin stability. As a result, a mutant *C. utilis* uricase enzyme containing these two substitutions was used a parent in the design of a second round of *C. utilis* uricases.

Unless otherwise indicated, the second round of mutational design, expression, purification, and pancreatin stability assays were all conducted as described above. The process resulted in 95 mutant *C. utilis* uricases each with five amino substitutions relative to the wild-type sequence, two of which in each case were the Y165F and I180V substitutions. The mutant *C. utilis* uricases are indicated as R2_V1-R2_V95 in TABLE 4.

TABLE 4 depicts the amino acid substitutions for the 95 mutant *C. utilis* uricases, as well as the specific activity (04/minute per 1.2 ng/µl of uricase), pancreatin stability (half-life, minutes) and expression yield (µg/ml) for each enzyme. Pancreatin stability was assayed at 80 ng/µL soluble pancreatin. "nd" indicates that activity and stability measurements were not determined due to insufficient expression yield.

TABLE 4

| Clone | Specific Activity* | Pancreatin Stability# | Expression (µg/ml) | Substitutions | | | | |
|---|---|---|---|---|---|---|---|---|
| R2 Parent | 4-4.9 | 30-49 | 200-299 | Y165F | I180V | | | |
| R2_V1 | 4-4.9 | 10-29 | >300 | Y165F | I180V | Q25A | T47E | S256D |
| R2_V2 | 4-4.9 | 30-49 | 200-299 | Y165F | I180V | D142Q | Q217L | A236N |
| R2_V3 | 4-4.9 | 30-49 | 200-299 | Y165F | I180V | G128P | R139E | D142E |
| R2_V4 | 4-4.9 | >50 | 200-299 | Y165F | I180V | E51K | V97I | A236N |
| R2_V5 | 3-3.9 | 0-9 | 200-299 | Y165F | I180V | E51K | F170Y | W271R |
| R2_V6 | 4-4.9 | 10-29 | 100-199 | Y165F | I180V | D134E | R139E | V296A |
| R2_V7 | 4-4.9 | 10-29 | 200-299 | Y165F | I180V | A87G | E220A | T224D |
| R2_V8 | 3-3.9 | 10-29 | >300 | Y165F | I180V | G44A | G128P | K270E |
| R2_V9 | 4-4.9 | 10-29 | 200-299 | Y165F | I180V | D142Q | I149L | F165Y |
| R2_V10 | 4-4.9 | 30-49 | >300 | Y165F | I180V | G44A | Y136R | Y253Q |
| R2_V11 | 3-3.9 | 0-9 | 200-299 | Y165F | I180V | I132R | S256D | W271R |
| R2_V12 | >5 | 30-49 | 100-199 | Y165F | I180V | E51K | I149L | D268N |
| R2_V13 | >5 | 0-9 | 200-299 | Y165F | I180V | D142E | Q174G | S254N |
| R2_V14 | 4-4.9 | >50 | 200-299 | Y165F | I180V | E92N | I149L | Y253Q |
| R2_V15 | 4-4.9 | >50 | 10-99 | Y165F | I180V | I132N | V190A | N213A |
| R2_V16 | 4-4.9 | 30-49 | 200-299 | Y165F | I180V | E51K | D142E | S256N |
| R2_V17 | 4-4.9 | >50 | 200-299 | Y165F | I180V | G44A | E51K | I132R |
| R2_V18 | 4-4.9 | 0-9 | >300 | Y165F | I180V | K103T | D134E | V180I |
| R2_V19 | 0-2.9 | 0-9 | 10-99 | Y165F | I180V | K85I | S147T | Q217L |
| R2_V20 | nd | nd | 0-9 | Y165F | I180V | E51K | Y137R | S254N |
| R2_V21 | 4-4.9 | 10-29 | 200-299 | Y165F | I180V | A52S | A236N | S256N |
| R2_V22 | 4-4.9 | 30-49 | >300 | Y165F | I180V | G128P | Y253Q | P285S |
| R2_V23 | 4-4.9 | 10-29 | 10-99 | Y165F | I180V | E51K | P118I | S147T |
| R2_V24 | 4-4.9 | 30-49 | 200-299 | Y165F | I180V | A84S | S140T | K204A |
| R2_V25 | 4-4.9 | 30-49 | >300 | Y165F | I180V | E51K | G128P | F170Y |
| R2_V26 | 4-4.9 | 30-49 | 100-199 | Y165F | I180V | E51K | A87G | D142Q |
| R2_V27 | 4-4.9 | 30-49 | 200-299 | Y165F | I180V | E51K | G128P | N213A |
| R2_V28 | 4-4.9 | 30-49 | 200-299 | Y165F | I180V | V97I | K103T | N213A |
| R2_V29 | 4-4.9 | 10-29 | 200-299 | Y165F | I180V | K103T | F165Y | K208A |
| R2_V30 | >5 | 30-49 | 200-299 | Y165F | I180V | Q25A | E51K | V296A |
| R2_V31 | 4-4.9 | 0-9 | 100-199 | Y165F | I180V | K85I | P118I | E220A |
| R2_V32 | 3-3.9 | 10-29 | 200-299 | Y165F | I180V | E51K | Y253Q | K270E |
| R2_V33 | nd | nd | 0-9 | Y165F | I180V | G128P | Y137R | A236N |
| R2_V34 | 4-4.9 | 10-29 | >300 | Y165F | I180V | Q25A | S95P | D142E |
| R2_V35 | 4-4.9 | 30-49 | >300 | Y165F | I180V | V97I | G128P | S140T |
| R2_V36 | 4-4.9 | 30-49 | 100-199 | Y165F | I180V | G128P | N193R | S254N |
| R2_V37 | 4-4.9 | 30-49 | 200-299 | Y165F | I180V | S95P | I132N | Y253Q |
| R2_V38 | 4-4.9 | 30-49 | >300 | Y165F | I180V | T47E | E92N | V97I |
| R2_V39 | 4-4.9 | >50 | >300 | Y165F | I180V | E51K | D142E | Q217L |
| R2_V40 | 3-3.9 | 10-29 | >300 | Y165F | I180V | A52S | K85I | Q244K |
| R2_V41 | 4-4.9 | 10-29 | 200-299 | Y165F | I180V | A84S | G128P | S256N |
| R2_V42 | 4-4.9 | 30-49 | >300 | Y165F | I180V | A84S | V97I | Y253Q |
| R2_V43 | 4-4.9 | 10-29 | 100-199 | Y165F | I180V | A87G | I196L | S256N |
| R2_V44 | nd | nd | 0-9 | Y165F | I180V | Y137R | D142Q | K204A |
| R2_V45 | 4-4.9 | >50 | >300 | Y165F | I180V | E51K | G128P | Y253Q |
| R2_V46 | 4-4.9 | 30-49 | >300 | Y165F | I180V | D142E | I196L | K208A |
| R2_V47 | 4-4.9 | >50 | >300 | Y165F | I180V | E51K | V97I | I196L |
| R2_V48 | 3-3.9 | 0-9 | >300 | Y165F | I180V | Q174G | T224D | Y253Q |
| R2_V49 | 4-4.9 | 30-49 | >300 | Y165F | I180V | I132R | D142E | V296A |
| R2_V50 | 3-3.9 | 0-9 | >300 | Y165F | I180V | G44A | D142E | W271R |
| R2_V51 | 4-4.9 | 30-49 | >300 | Y165F | I180V | V97I | D142E | Y253Q |
| R2_V52 | 4-4.9 | 30-49 | 200-299 | Y165F | I180V | A84S | D142E | V190A |
| R2_V53 | 4-4.9 | 30-49 | 200-299 | Y165F | I180V | E92N | F170Y | N193R |
| R2_V54 | 3-3.9 | 0-9 | >300 | Y165F | I180V | G128P | V180I | Q217L |

TABLE 4-continued

| Clone | Specific Activity* | Pancreatin Stability# | Expression (µg/ml) | Substitutions | | | | |
|---|---|---|---|---|---|---|---|---|
| R2_V55 | 4-4.9 | 30-49 | 200-299 | Y165F | I180V | V97I | F170Y | S254N |
| R2_V56 | 3-3.9 | 30-49 | >300 | Y165F | I180V | E92N | G128P | D142E |
| R2_V57 | 4-4.9 | 10-29 | 100-199 | Y165F | I180V | A52S | I196L | S254N |
| R2_V58 | 4-4.9 | 10-29 | 200-299 | Y165F | I180V | S140T | T224D | S256N |
| R2_V59 | 4-4.9 | 10-29 | >300 | Y165F | I180V | S95P | K103T | G128P |
| R2_V60 | 4-4.9 | 30-49 | >300 | Y165F | I180V | Y136R | Q244K | L274I |
| R2_V61 | 4-4.9 | >50 | 200-299 | Y165F | I180V | A84S | Q217L | Q244K |
| R2_V62 | 4-4.9 | 10-29 | >300 | Y165F | I180V | S95P | S140T | L274I |
| R2_V63 | 4-4.9 | 30-49 | >300 | Y165F | I180V | D142E | N193R | L274I |
| R2_V64 | 4-4.9 | 30-49 | >300 | Y165F | I180V | G44A | K204A | P285S |
| R2_V65 | 0-2.9 | 10-29 | 10-99 | Y165F | I180V | V97I | D134E | Y137R |
| R2_V66 | 4-4.9 | 10-29 | 100-199 | Y165F | I180V | A52S | E92N | S256D |
| R2_V67 | nd | nd | 0-9 | Y165F | I180V | D142E | F165Y | P285S |
| R2_V68 | 4-4.9 | 30-49 | 100-199 | Y165F | I180V | V97I | I132N | T224D |
| R2_V69 | 4-4.9 | 10-29 | 100-199 | Y165F | I180V | F170Y | Q217L | D268N |
| R2_V70 | 4-4.9 | 30-49 | 200-299 | Y165F | I180V | ]S95P | Q217L | S254N |
| R2_V71 | 4-4.9 | 30-49 | >300 | Y165F | I180V | G44A | S95P | V97I |
| R2_V72 | 3-3.9 | 10-29 | 100-199 | Y165F | I180V | D142E | S147T | F170Y |
| R2_V73 | 4-4.9 | 10-29 | >300 | Y165F | I180V | S140T | F165Y | A236N |
| R2_V74 | 4-4.9 | 10-29 | 100-199 | Y165F | I180V | V97I | K208A | D268N |
| R2_V75 | 4-4.9 | 30-49 | >300 | Y165F | I180V | V97I | G128P | V190A |
| R2_V76 | 4-4.9 | 0-9 | 100-199 | Y165F | I180V | Y136R | N193R | K270E |
| R2_V77 | 4-4.9 | 30-49 | >300 | Y165F | I180V | Q25A | G128P | I149L |
| R2_V78 | 4-4.9 | 10-29 | >300 | Y165F | I180V | V97I | P118I | D142E |
| R2_V79 | 4-4.9 | >50 | 200-299 | Y165F | I180V | I132R | Q217L | P285S |
| R2_V80 | 3-3.9 | 30-49 | >300 | Y165F | I180V | T47E | I196L | Y253Q |
| R2_V81 | 4-4.9 | 30-49 | 200-299 | Y165F | I180V | E51K | Y136R | V190A |
| R2_V82 | 3-3.9 | 0-9 | 100-199 | Y165F | I180V | E92N | V180I | D268N |
| R2_V83 | nd | nd | 0-9 | Y165F | I180V | I132N | R139E | E220A |
| R2_V84 | 4-4.9 | 30-49 | 100-199 | Y165F | I180V | A87G | K204A | L274I |
| R2_V85 | 0-2.9 | 0-9 | 10-99 | Y165F | I180V | V97I | S147T | K270E |
| R2_V86 | 4-4.9 | 0-9 | 100-199 | Y165F | I180V | R139E | Q174G | Q244K |
| R2_V87 | 4-4.9 | 30-49 | 200-299 | Y165F | I180V | A84S | A236N | V296A |
| R2_V88 | 0-2.9 | 0-9 | >300 | Y165F | I180V | T47E | G128P | W271R |
| R2_V89 | 4-4.9 | 30-49 | 100-199 | Y165F | I180V | E51K | K85I | P285S |
| R2_V90 | 4-4.9 | 0-9 | >300 | Y165F | I180V | V180I | Y253Q | S256D |
| R2_V91 | 4-4.9 | >50 | >300 | Y165F | I180V | E51K | S140T | D142E |
| R2_V92 | 4-4.9 | 30-49 | 100-199 | Y165F | I180V | V97I | E220A | S256N |
| R2_V93 | 4-4.9 | 0-9 | >300 | Y165F | I180V | Q174G | N213A | P285S |
| R2_V94 | 4-4.9 | 10-29 | >300 | Y165F | I180V | P118I | G128P | I196L |
| R2_V95 | 4-4.9 | 30-49 | >300 | Y165F | I180V | D134E | K208A | Y253Q |

Figure 4:
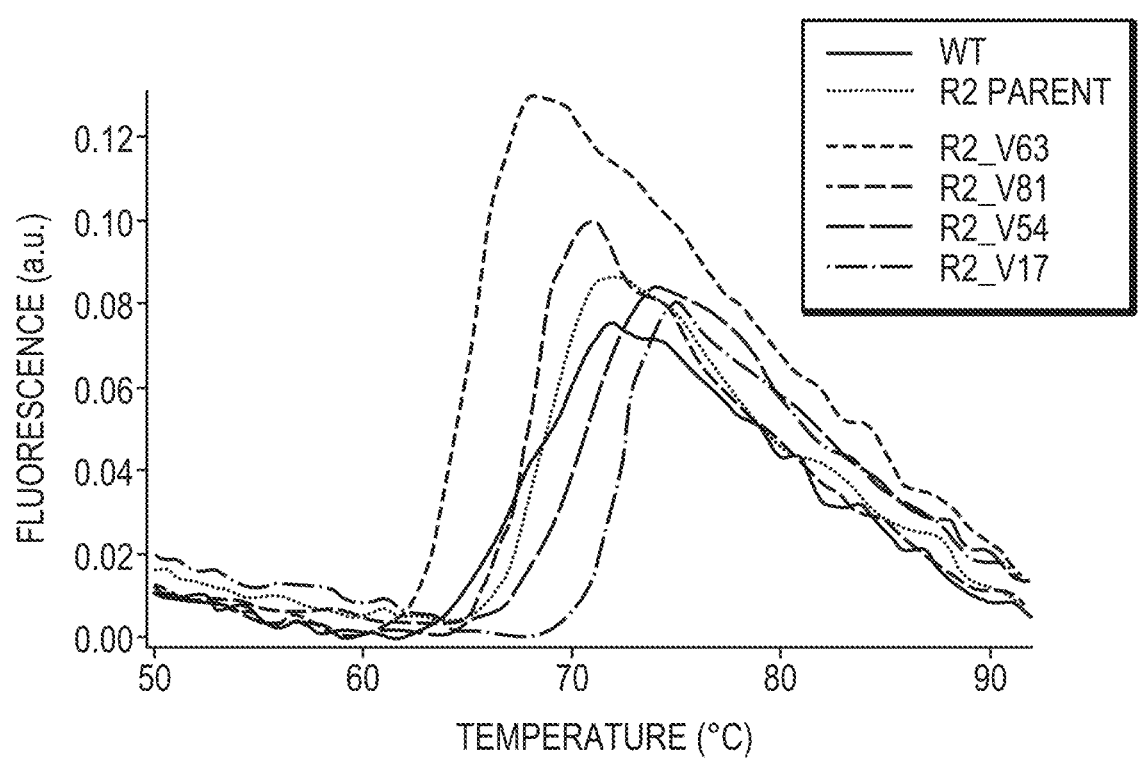
FIG. 4 shows protein unfolding as determined by differential scanning fluorimetry (DSF) for wild-type C. utilis uricase and the indicated mutant C. utilis uricase enzymes.

*Specific Activity unit: µM/min per 1.2 ng/µl of uricase; #Pancreatin stability unit: half-life, minutes Representative pancreatin stability data for a subset of the mutant C. utilis uricases is depicted in FIG. 3. A subset of mutant C. utilis uricases were further tested for thermal stability by differential scanning fluorimetry (DSF). DSF is a method to evaluate thermal stability by heating a protein in the presence of a fluorescent dye which will increase its fluorescence upon binding to the exposed hydrophobic interior of the protein after protein unfolding. Protein unfolding curves are depicted in FIG. 4. As can be seen, R2_V17 has the highest melting temperature among those tested, with a 5° C. increase relative to wild type uricase.

Figure 5:
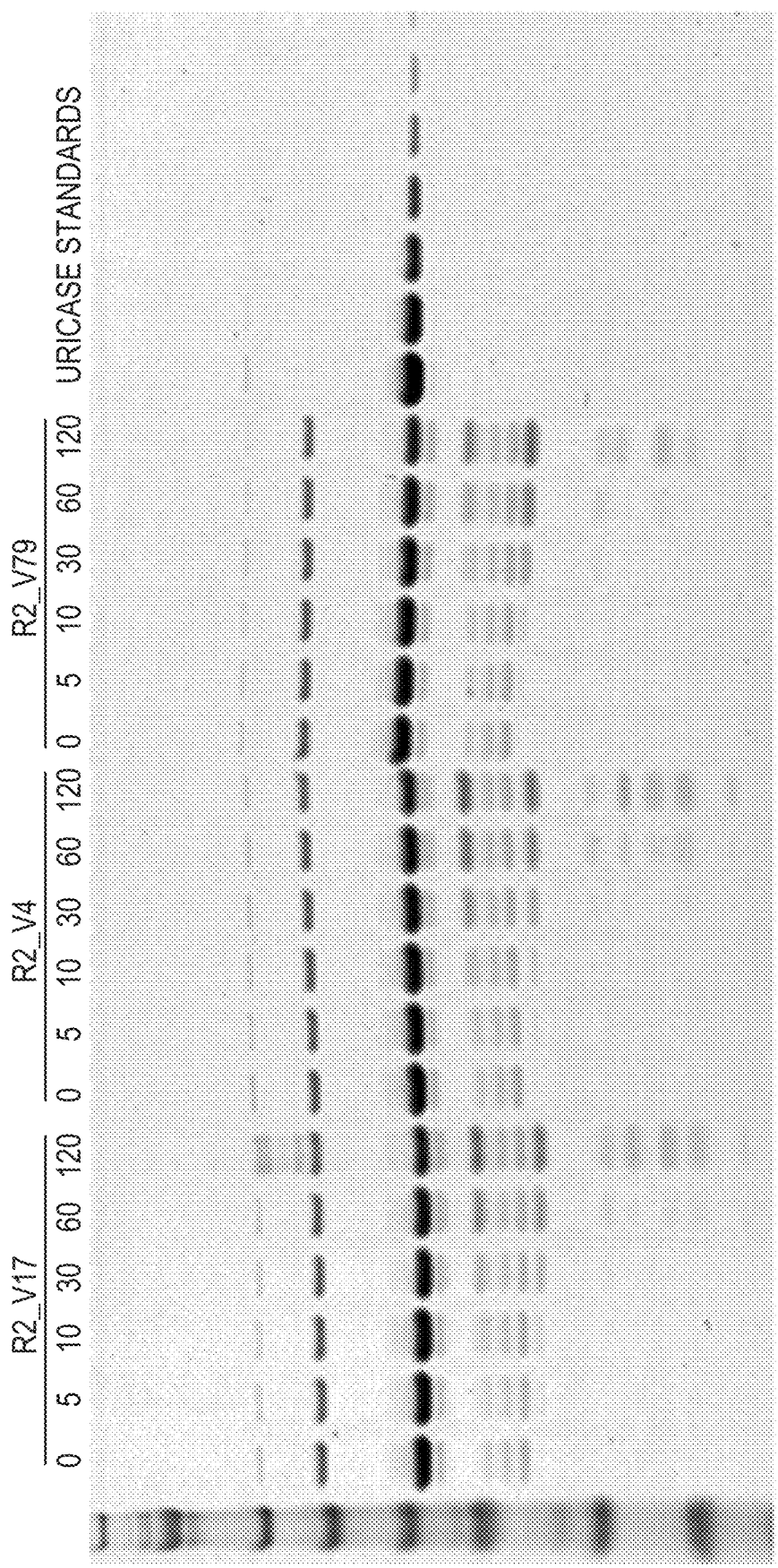
FIG. 5 is an SDS-PAGE gel showing the R2_V17, R2_V4 and R2_V79 mutant C. utilis uricases following incubation with pancreatin for the indicated timepoints.
Figure 6:
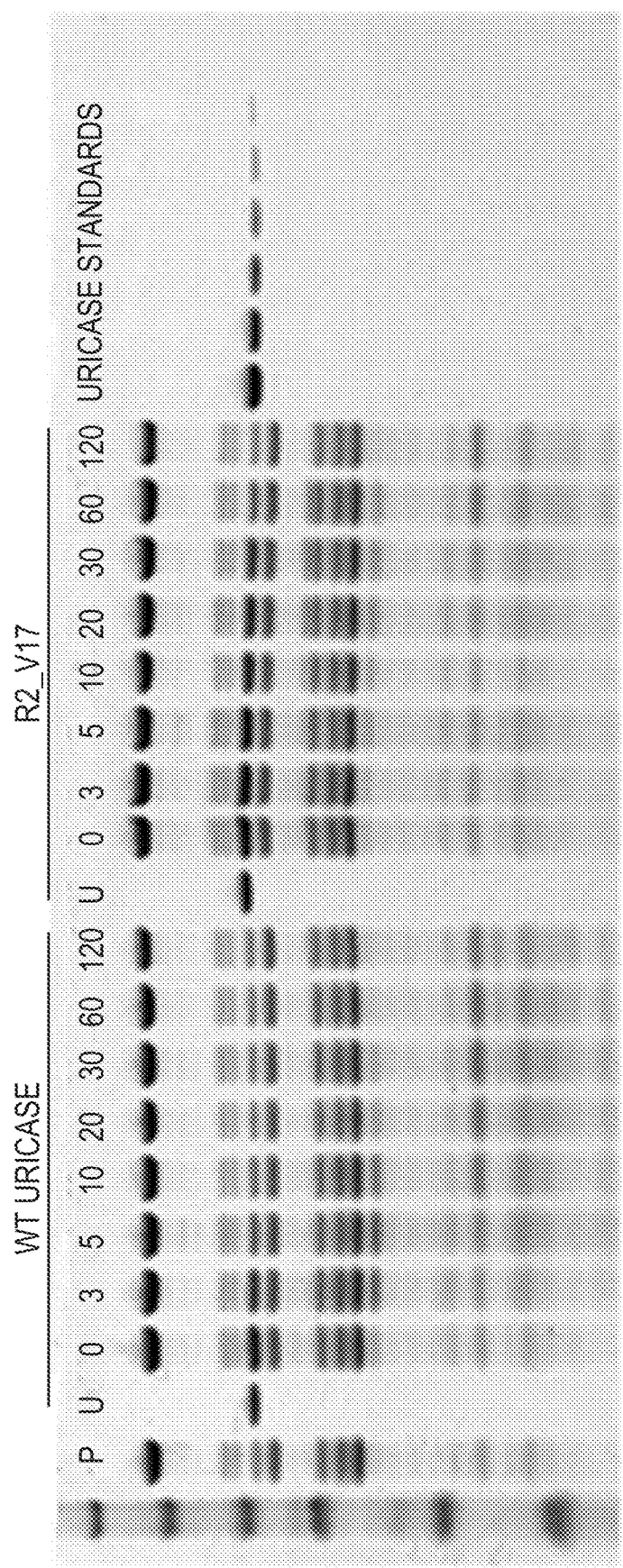
FIG. 6 is an SDS-PAGE gel showing the wild-type C. utilis uricase and R2_V17 mutant C. utilis uricase following incubation with pancreatin for the indicated timepoints.

A subset of mutant C. utilis uricase enzymes were further tested for pancreatin stability by SDS-PAGE. FIG. 5 shows the analysis of R2_V17, R2_V4, and R2_V79 C. utilis uricase enzymes by SDS-PAGE following incubation of 144 ng/µL of uricase with 80 ng/µL of pancreatin in SIF buffer at 37° C. for the indicated time points. FIG. 6 shows the analysis of wild type and R2_V17 C. utilis uricase enzymes by SDS-PAGE following incubation of 100 ng/µL of uricase with 320 ng/µL of pancreatin in SIF buffer at 37° C. for the indicated time points. The results from the SDS-PAGE analysis are consistent with the activity assay data. In particular, the R2_V17, R2_V4 and R2_V79 mutants show increased stability in the presence of pancreatin relative to wild type.

Together, these results identify mutant C. utilis uricase enzymes with increased stability against pancreatin compared to the wild-type C. utilis uricase and without significantly decreased specific activity.

Example 2—Identification of Individual Substitutions that Improve Candida utilis Uricase Stability This example describes the testing of individual substitutions included in the recombinant mutant Candida utilis uricases described in Example 1.

Figure 7:
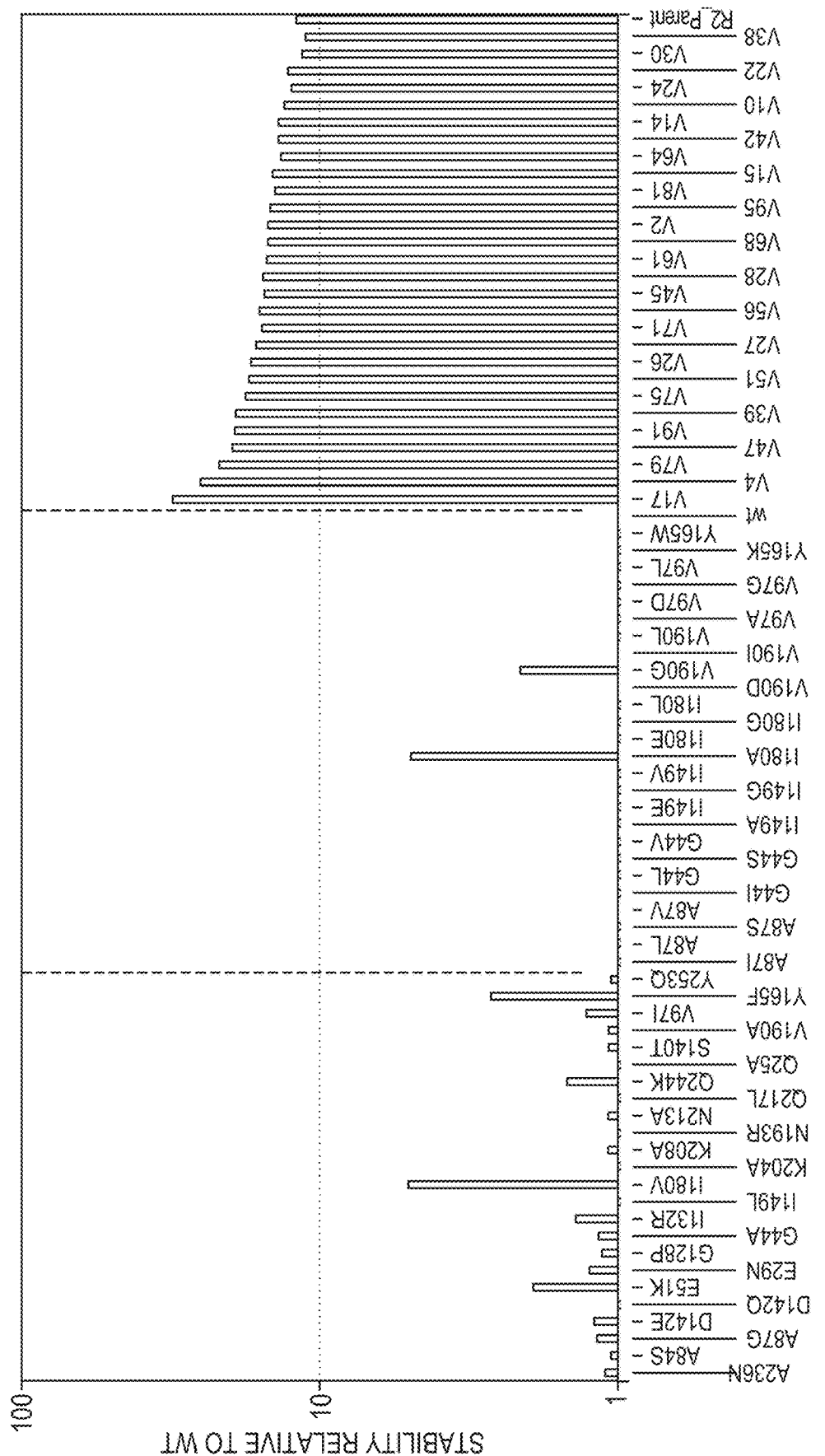
FIG. 7 is a bar graph showing the pancreatin stability of the indicated mutant C. utilis uricases relative to wild-type. R2 mutant C. utilis uricases described in Example 1, each containing five substitutions (right), and mutant C. utilis uricases described in Example 2, each containing a single substitution (left and middle), are depicted.
Figure 8:
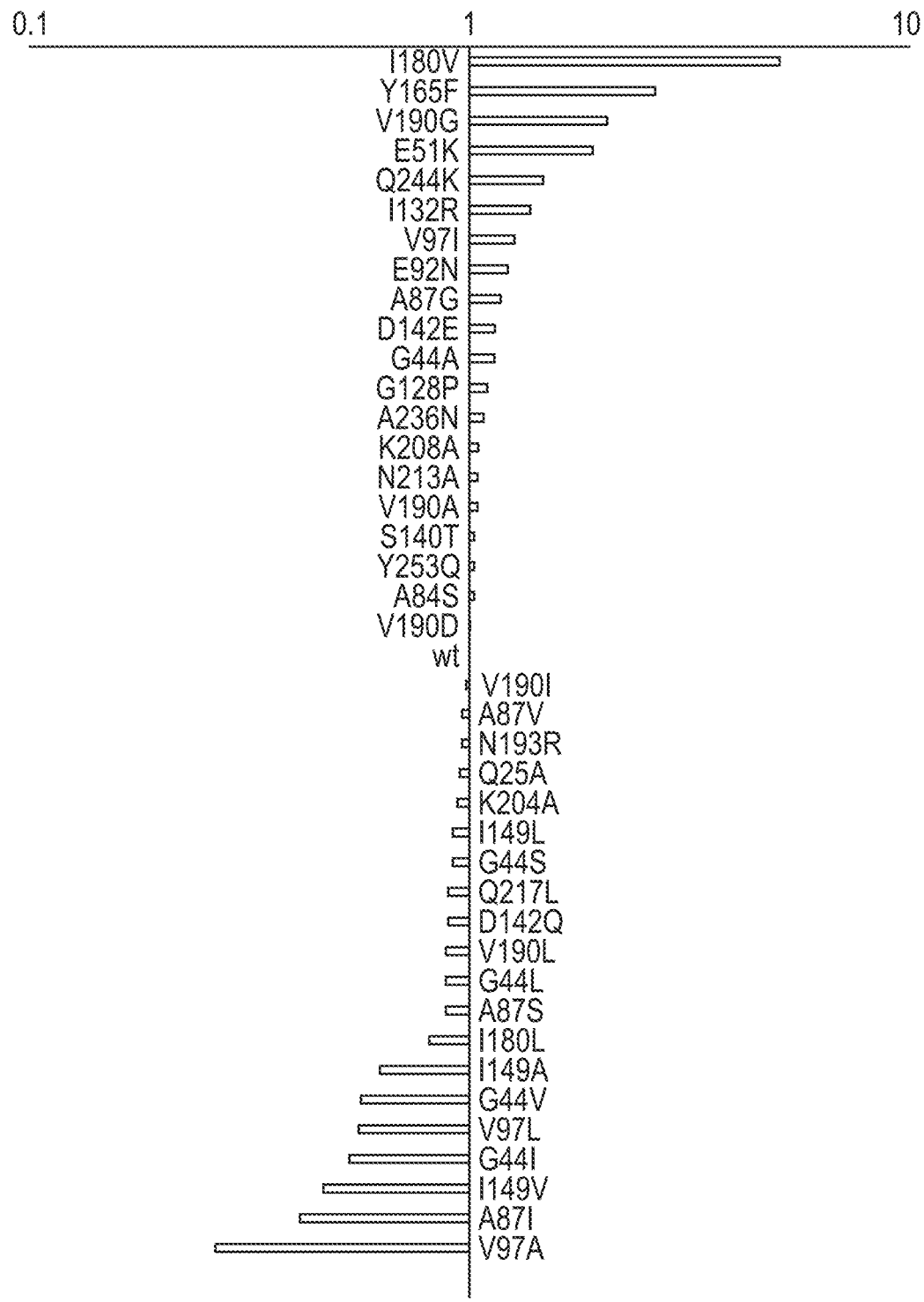
FIG. 8 is a waterfall chart showing the pancreatin stability of the mutant C. utilis uricases described in Example 2, each containing a single substitution, relative to wild-type. Enzymes are ordered relative to their effect on stability.

Among the various substitutions included in the mutant Candida utilis uricases described in Example 1, a set of individual substitutions were selected for testing by protein modeling tools. In certain instances, conservative substitutions were tested along with the original substitution that was identified in Example 1. In total, 51 mutant C. utilis uricases, each with one amino acid substitution relative to the wild-type sequence, were designed and tested. The 51 mutant C. utilis uricases containing one amino acid substitution are indicated by the individual substitution in TABLE 5. The mutant C. utilis uricases were tested in a pancreatin stability assay along with a subset of the mutant C. utilis uricases described in Example 1. The subset of mutant C. utilis uricases described in Example 1 that were tested, containing five substitutions, are as set forth in TABLE 3. Results are summarized in TABLE 5, FIG. 7, and FIG. 8.

TABLE 5 depicts the amino acid substitutions for the mutant *C. utilis* uricases, as well as the specific activity (04/minute per 1.204 of uricase), pancreatin stability (half-life, minutes.±SEM), and expression yield (μg/ml) for each enzyme. Pancreatin stability was assayed at 40 ng/μL soluble pancreatin. "nd" indicates that activity and stability measurements were not determined due to insufficient expression yield.

TABLE 5

| Clone | Pancreatin Stability (half-life, minutes) | Expression (μg/ml) | Specific Activity (μM/minute per 1.2 μM of uricase) |
| --- | --- | --- | --- |
| R2_V17 | >125 | 200-299 | 100-124 |
| R2_V4 | >125 | 200-299 | >150 |
| R2_V79 | >125 | 100-199 | 0-99 |
| R2_V47 | >125 | 200-299 | 125-149 |
| R2_V91 | >125 | >300 | 100-124 |
| R2_V39 | >125 | 200-299 | 0-99 |
| R2_V75 | >125 | 200-299 | 125-149 |
| R2_V51 | >125 | >300 | 125-149 |
| R2_V26 | 100-124 | 100-199 | 125-149 |
| R2_V27 | 100-124 | 200-299 | 125-149 |
| R2_V71 | 100-124 | >300 | 100-124 |
| R2_V56 | 100-124 | >300 | 100-124 |
| R2_V45 | 100-124 | 200-299 | 100-124 |
| R2_V28 | 100-124 | 200-299 | 125-149 |
| R2_V61 | 100-124 | 200-299 | 100-124 |
| R2_V68 | 100-124 | 10-99 | 125-149 |
| R2_V2 | 100-124 | 200-299 | 100-124 |
| R2_V95 | 100-124 | 200-299 | 125-149 |
| R2_V81 | 100-124 | 100-199 | 125-149 |
| R2_V15 | 50-99 | 10-99 | 125-149 |
| R2_V64 | 50-99 | >300 | 125-149 |
| R2_V42 | 50-99 | >300 | 100-124 |
| R2_V14 | 50-99 | 100-199 | 125-149 |
| R2_V10 | 50-99 | 200-299 | 100-124 |
| R2_V24 | 50-99 | 200-299 | 0-99 |
| R2_V22 | 50-99 | >300 | 125-149 |
| R2_Parent | 50-99 | >300 | 125-149 |
| R2_V30 | 50-99 | 200-299 | 125-149 |
| R2_V38 | 50-99 | 200-299 | 100-124 |
| I180V | 10-49 | 200-299 | 125-149 |
| I180A | 10-49 | 10-99 | >150 |
| Y165F | 10-49 | 200-299 | 0-99 |
| V190G | 10-49 | 100-199 | 100-124 |
| E51K | 10-49 | 200-299 | 125-149 |
| Q244K | 10-49 | 200-299 | 125-149 |
| I132R | 5-9.9 | 100-199 | 125-149 |
| V97I | 5-9.9 | 200-299 | 125-149 |
| E92N | 5-9.9 | 200-299 | 125-149 |
| A87G | 5-9.9 | 200-299 | 125-149 |
| D142E | 5-9.9 | >300 | 125-149 |
| G44A | 5-9.9 | >300 | 100-124 |
| G128P | 5-9.9 | >300 | 100-124 |
| A236N | 5-9.9 | >300 | 100-124 |
| K208A | 5-9.9 | >300 | 100-124 |
| N213A | 5-9.9 | 200-299 | 125-149 |
| V190A | 5-9.9 | 200-299 | 125-149 |
| S140T | 5-9.9 | >300 | 125-149 |
| Y253Q | 5-9.9 | 200-299 | 125-149 |
| A84S | 5-9.9 | >300 | 125-149 |
| V190D | 5-9.9 | 200-299 | 125-149 |
| WT | 5-9.9 | >300 | 100-124 |
| V190I | 5-9.9 | 200-299 | 125-149 |
| A87V | 5-9.9 | 200-299 | 125-149 |
| N193R | 5-9.9 | >300 | 100-124 |
| Q25A | 5-9.9 | >300 | 125-149 |
| K204A | 5-9.9 | 200-299 | 125-149 |
| I149L | 5-9.9 | >300 | 100-124 |
| G44S | 5-9.9 | 200-299 | 125-149 |
| Q217L | 5-9.9 | 200-299 | >150 |
| D142Q | 5-9.9 | 200-299 | 125-149 |
| V190L | 5-9.9 | 200-299 | 100-124 |
| G44L | 5-9.9 | 200-299 | >150 |
| A87S | 5-9.9 | 200-299 | 125-149 |
| I180L | 5-9.9 | 200-299 | 125-149 |
| I149A | 0-4.9 | 10-99 | 125-149 |
| G44V | 0-4.9 | 200-299 | 125-149 |
| V97L | 0-4.9 | 200-299 | 125-149 |
| G44I | 0-4.9 | 200-299 | 125-149 |
| I149V | 0-4.9 | 10-99 | 100-124 |
| A87I | 0-4.9 | 10-99 | 125-15 |
| V97A | 0-4.9 | 100-199 | 100-124 |
| I180G | nd | 10-99 | nd |
| Y165W | 0-4.9 | 100-199 | 0-99 |
| V97G | nd | 10-99 | nd |
| A87L | nd | 0-9 | nd |
| I149E | nd | 0-9 | nd |
| Y165K | 0-4.9 | 200-299 | 0-99 |
| I180E | nd | 10-99 | nd |
| V97D | nd | 0-9 | nd |
| I149G | nd | 0-9 | nd |

Together, these results identify mutant *C. utilis* uricases with increased stability against pancreatin compared to the wild-type *C. utilis* uricase and without significantly decreased specific activity, and identify single substitutions that are sufficient to increase *C. utilis* uricase stability.

Example 3—Recombinant Mutant *Candida utilis* Uricase Reduces Severe Hyperuricemia and Normalizes Hyperuricosuria in Nephropathic UrOx Knockout (UrOxKO) Mice In this example, the effect of targeted gut elimination of urate (uric acid) by oral administration of recombinant mutant *Candida utilis* uricase on hyperuricemia (excessive amounts of urate in blood) and hyperuricosuria (excessive amounts of uric acid in urine) was investigated. The UrOxKO mice, generated with a targeted mutation at the urate oxidase locus by gene targeting in ES cells (following the method described in Wu et al., Proc. Nat. Acad. Sci. USA (1994), 91:742-746), develop severe hyperuricemia, hyperuricosuria, and uric acid crystalline obstructive nephropathy, and, therefore, is a suitable model to investigate hyperuricemia and associated disorders mimicking the human conditions.

An expression vector comprising a codon-optimized nucleic acid sequence of SEQ ID NO: 13, which encodes a mutant *Candida utilis* uricase, was expressed in *E. coli*, and the expressed recombinant mutant uricase was isolated and purified.

(SEQ ID NO: 13)
ATGAGCACCACACTGAGCAGCAGCACCTATGGTAAAGATAATGTGAAATT

CCTGAAAGTGAAAAAAGATCCGCAGAACCCGAAAAAACAAGAAGTTATGG

AAGCAACCGTTACCTGTCTGCTGGAAGGTGCATTTGATACCAGCTATACC

AAAGCAGATAATAGCAGCATTGTTCCGACCGATACCGTGAAAAATACCAT

TCTGGTTCTGGCAAAAACCACCGAAATTTGGCCGATTGAACGTTTTGCAG

CCAAACTGGCAACCCATTTTGTTGAGAAATATTCTCATGTTAGCGGTGTG

AGCGTTAAAATTGTTCAGGATCGTTGGGTTAAATATGCCGTTGATGGTAA

ACCGCATGATCACAGCTTTATTCATGAAGGTGGTGAAAAACGTCGTACCG

ATCTGTATTACAAACGTAGCGGTGATTATAAACTGTCCAGCGCAATTAAA

-continued

```
GATCTGACCGTTCTGAAAAGCACCGGCAGCATGTTTTATGGTTTTAACAA

ATGCGATTTCACAACCCTGCAGCCGACCACCGATCGTGTTCTGAGCACCG

ATGTTGATGCAACCTGGGTTTGGGATAATAAGAAAATTGGTAGCGTGTAC

GATATTGCCAAAGCAGCAGATAAAGGCATCTTCGATAATGTGTATAATCA

GGCACGTGAAATTACCCTGACCACCTTTGCACTGGAAAATAGCCCGAGCG

TTCAGGCAACCATGTTTAATATGGCGACCCAGATTCTGGAAAAAGCGTGT

AGCGTTTATAGCGTTAGCTATGCACTGCCGAACAAACACTATTTTCTGAT

TGACCTGAAATGGAAGGGCCTTGAAAATGATAACGAACTGTTTTATCCGA

GTCCGCATCCGAATGGTCTGATTAAATGTACCGTTGTGCGTAAAGAGAAA

ACCAAACTG
```

The study used UrOxKO mice in three parallel arms in three study periods—a pre-treatment arm, a treatment arm, and a follow-up arm, each lasting 7 days. All mice received 150 mg/L allopurinol (ALLO) prior to initiation of the study; this phase is the maintenance dose of ALLO. During the "pre-treatment" period the mice were not administered the maintenance dose of ALLO or any other therapeutic agent for treating severe hyperuricemia, hyperuricosuria, and uric acid crystalline obstructive nephropathy.

Eight (8) mice were selected in the treatment arm for treatment with recombinant mutant uricase, and, as a positive control, seventeen (17) mice were selected for treatment with allopurinol (ALLO) (n=9 for ALLO 150 mg/L, and n=8 for ALLO 50 mg/L); measurements of plasma urate levels were taken from the same group of mice (i.e., closed cohort) before starting treatment (on day 7 of removal of ALLO maintenance dose, or day 7 of the pre-treatment period), during treatment (on day 7 of treatment (spray dried powder of 25% Uricase and 75% trehalose, mixed with 3.5 g food, was administered each day for 7 days, and measurements were taken on day 7 of the treatment)), and in the follow-up arm, 7 days after termination of treatment. In both the recombinant mutant uricase and ALLO cohorts, mice received a maintenance dose of 150 mg/L ALLO before initiation of the respective pre-treatment observation period.

At the start of the pre-treatment period, the maintenance dose of 150 mg/L ALLO was removed. The plasma urate levels were measured in plasma samples collected on day 7 after removal of the maintenance dose of ALLO, and urine uric acid levels were measured in 24-hour urine samples collected during the last 3 days of the pre-treatment period. Plasma urate levels and urine uric acid levels were measured following the Liquick Cor-UA 30 plus protocol by Cormay, Poland (Liquick Cor-UA 30 plus, kit size 5×30 ml, Cat. No. 2-260.

Mice treated with the recombinant mutant uricase (n=8) orally received approximately 62 mg/day (or 1,500 U/day) recombinant mutant uricase mixed with food (spray dried powder of 25% Uricase and 75% trehalose, mixed with 3.5 g food). In the control group, mice (n=17) were administered 150 mg/L of ALLO (n=9) and 50 mg/L of ALLO (n=8), supplemented in water. The plasma urate levels were measured in blood samples collected from the mice on day 7 of treatment with recombinant mutant uricase, ALLO 150 mg/L, and ALLO 50 mg/L, respectively, and urine uric acid levels were measured in 24-hour urine samples collected during the last 3 days of the treatment period.

In the follow-up period, plasma urate levels were measured in blood samples collected from the mice on day 7 after termination of treatment with recombinant mutant uricase, ALLO 150 mg/L, and ALLO 50 mg/L, respectively.

The assay for urine uric acid was performed according to the manufacturer's instructions (Liquick Cor-UA 30 plus protocol by Cormay, Poland (Liquick Cor-UA 30 plus, kit size 5×30 ml, Cat. No. 2-260)). For example, urine samples were diluted 1:4, 1:9, or 1:14 depending on groups of animals and the time of collection. To prevent precipitation of salts of uric acid, 1 drop of NaOH (500 g/L) was added to the collection tube before collection of a 24-hour specimen.

Plasma urate levels were also measured according to manufacturer's instructions (Liquick Cor-UA 30 plus protocol). Urate levels in the blood samples were measured without dilution or diluted 1:1 with double-distilled water ($ddH_2O$).

Figure 9A:
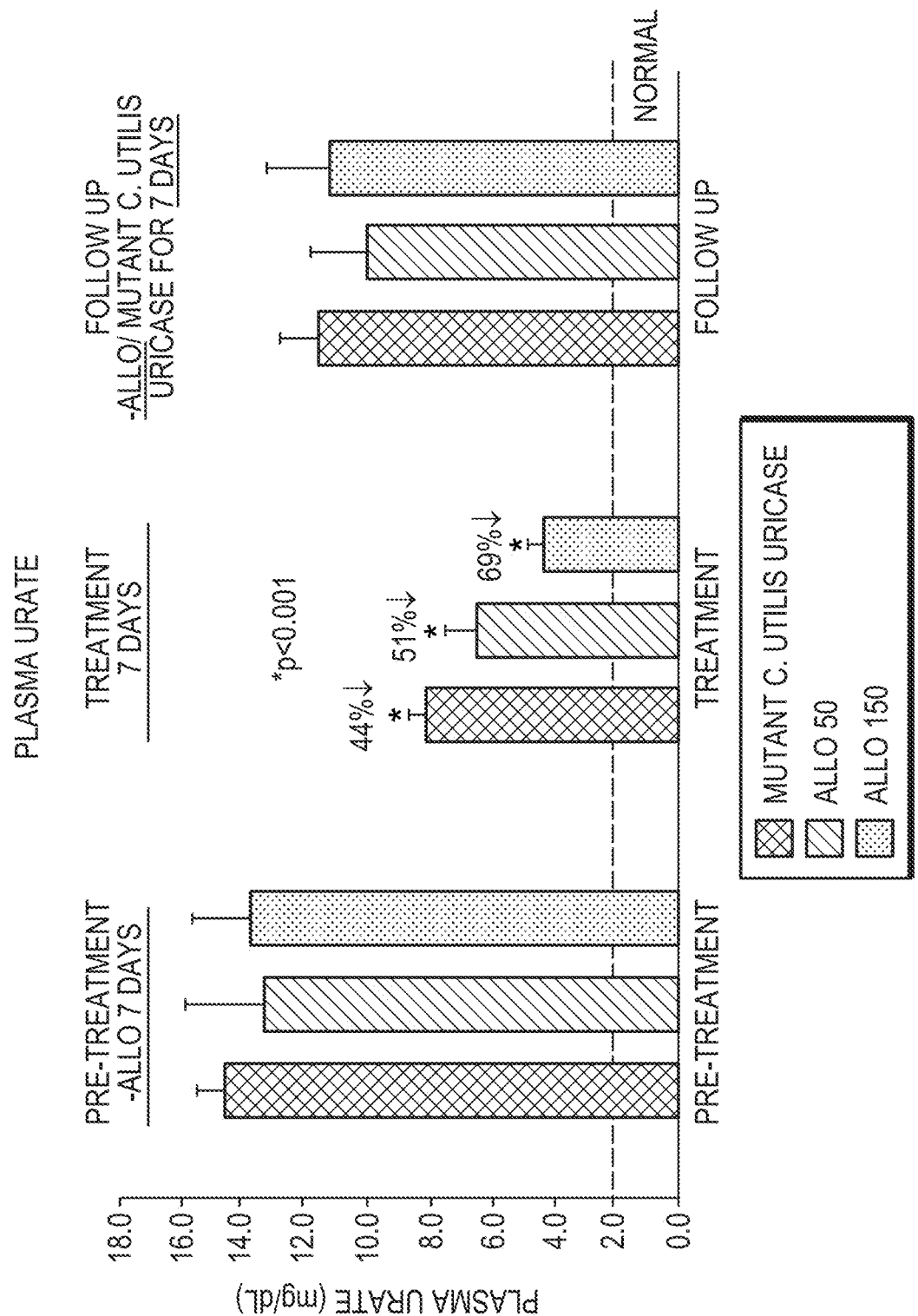
FIG. 9A is a bar graph showing the plasma urate levels (mg/dL) in Uricase knockout (UrOxKO) mice with severe hyperuricemia. Mean (SEM) of pre-treatment (plasma urate level was measured in samples collected on day 7 after removal of maintenance dose of allopurinol), treatment (plasma urate level was measured in samples collected on day 7 after administration of 50 mg/L of allopurinol, 150 mg/L of allopurinol, or 150 mg/day mutant C. utilis uricase, respectively), and post-treatment (plasma urate level was measured in samples collected on day 7 after treatment was terminated) plasma urate levels are shown.
Figure 9B:
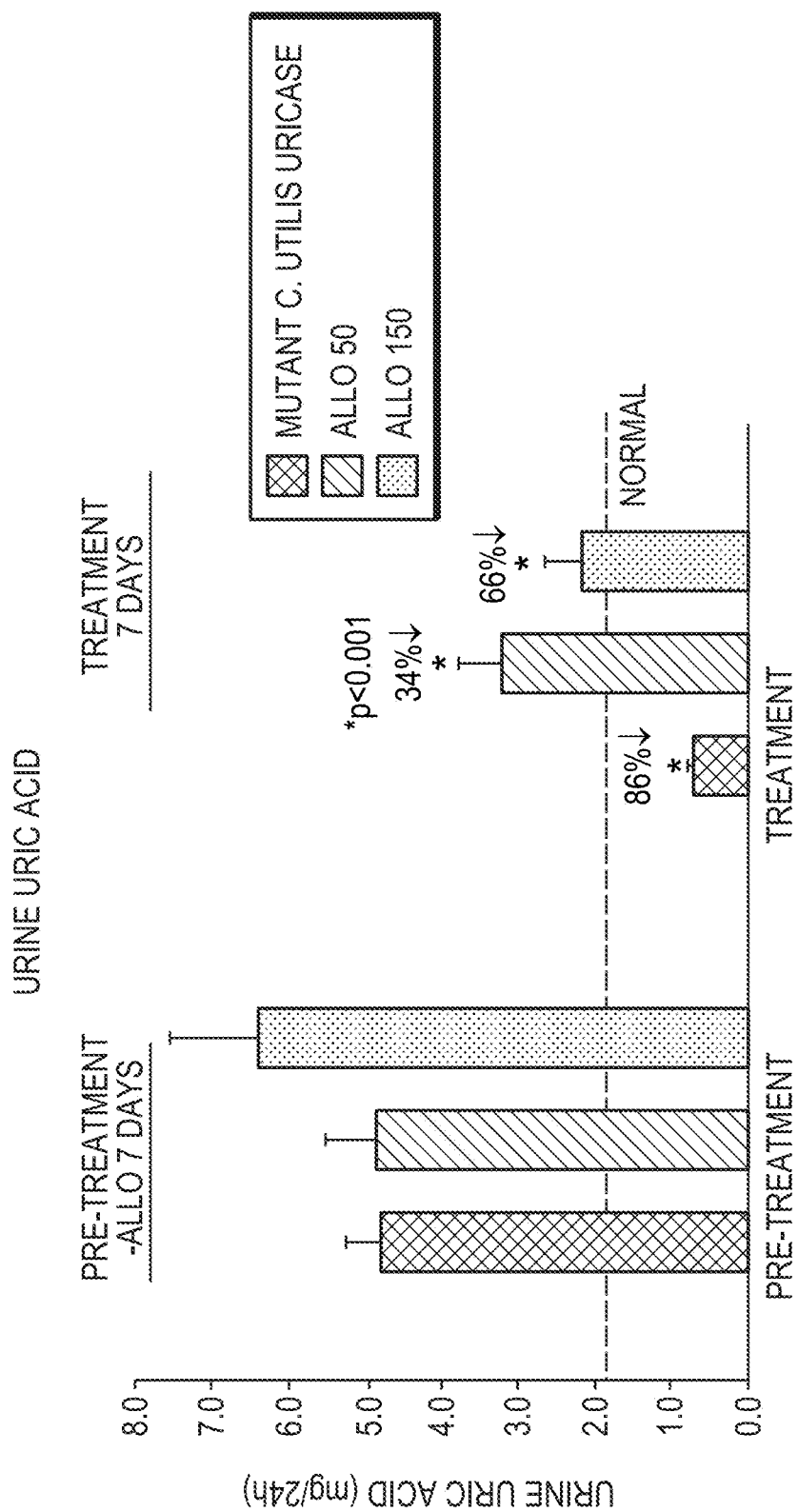
FIG. 9B is a bar graph showing the urine uric acid levels (mg/dL) in UrOxKO mice with severe hyperuricosuria. Uric acid levels were measured in 24-hour urine samples collected during the last 3 days of pre-treatment and treatment periods, as indicated.

The measured plasma urate levels and the urine uric acid levels demonstrated that hyperuricemia (i.e., excess of uric acid in the blood) was reduced significantly ($p<0.001$) and hyperuricosuria (i.e., the presence of excessive amounts of uric acid in the urine) normalized in 7 days after oral administration of the recombinant mutant uricase (FIGS. 9A and 9B). Mice treated with recombinant mutant uricase had a plasma urate decrease by 44% from pre-treatment (standard of mean (SEM) 14.5±0.9 to 8.1±0.5 mg/dL), which was similar to 51% decrease observed in the 50 mg/L ALLO mice (mean (SEM) 13.2±2.6 to 6.5±1.1 mg/dL); p=NS. The result demonstrated that there was no significant difference between the effects of ALLO 50 mg/L and recombinant mutant uricase on plasma urate levels. The highest reduction of 69% was observed in mice treated with ALLO 150 mg/L (mean (SEM) 13.8±1.7 to 4.3±0.6 mg/dL).

The removal of recombinant mutant uricase or ALLO resulted in hyperuricemia returning to approximately the pre-treatment levels. This was studied as follows.

Urine uric acid excretion normalized (<2 mg/24 hour) with recombinant mutant uricase with 86% reduction (mean (SEM) 4.7±0.6 to 0.7±0.1 mg/24 h); while in mice treated with ALLO 50 mg/L and 150 mg/L, reduction was 34% (mean (SEM) 4.9±0.4 to 3.2±0.3 mg/24 h) and 66% (mean (SEM) 6.4±0.7 to 2.2±0.3 mg/24 h), respectively. Analysis of digesta (the semifluid mass into which food is converted by gastric secretion and which passes from the stomach into the small intestine) from different parts of the gastrointestinal tract (GIT) indicated the uric acid is present along the whole gut, confirming secretion of the urate from circulation.

The results presented in this example demonstrated that targeting enteric uric acid (uric acid secrete from circulation into intestine), by orally administered recombinant mutant uricase successfully lowered serum uric acid level, and normalized urinary uric acid in nephropathic UrOxKO mice.

NUMBERED EMBODIMENTS

It is to be understood that while the present disclosure has been described in conjunction with the detailed description thereof, the foregoing description is intended to illustrate and not limit the scope of the disclosure, which is presented by the scope of the appended claims. Other aspects, advantages, and modifications are within the scope of the following claims.

Embodiments disclosed herein include embodiments P1 to P53, as provided in the numbered embodiments of the disclosure:

Embodiment P1

A recombinant mutant *Candida utilis* uricase comprising at least one (for example, one, two, three, four, five, six, seven or eight) mutation(s) at a position corresponding to wild type *C. utilis* uricase of SEQ ID NO: 1, wherein the at least one mutation is selected from: (a) at position 180, isoleucine is substituted by valine or alanine (I180V or I180A), (b) at position 165, tyrosine is substituted by phenylalanine (Y165F), (c) at position 190, valine is substituted by glycine or alanine (V190G or V190A), (d) at position 51, glutamic acid is substituted by lysine (E51K), (e) at position 244, glutamine is substitute by lysine (Q244K), (f) at position 132, isoleucine is substituted by arginine or asparagine (I132R or I132N), (g) at position 97, valine is substituted by isoleucine (V97I), (h) at position 92, glutamic acid is substituted by asparagine (E92N), (i) at position 87, alanine is substituted by glycine (A87G), (j) at position 142, aspartic acid is substituted by glutamic acid (D142E), (k) at position 44, glycine is substituted by alanine (G44A), (l) at position 128, glycine is substituted by proline (G128P), (m) at position 236, alanine is substituted by asparagine (A236N), (n) at position 208, lysine is substituted by alanine (K208A), (o) at position 213, asparagine is substituted by alanine (N213A), (p) at position 140, serine is substituted by threonine (S140T), (q) at position 253, tyrosine is substituted by glutamine (Y253Q), (r) at position 84, alanine is substituted by serine (A84S), (s) at position 47, threonine is substituted by glutamic acid (T47E), (t) at position 95, serine is substituted by proline (S95P), (u) at position 103, lysine is substituted by threonine (K103T), (v) at position 134, aspartic acid is substituted by glutamic acid (D134E), (w) at position 136, tyrosine is substituted by arginine (Y136R), (x) at position 196, isoleucine is substituted by leucine (I196L), (y) at position 224, threonine is substituted by aspartic acid (T224D), (z) at position 285, proline is substituted by serine (P285S), and (aa) at position 296, valine is substituted by alanine (V296A).

Embodiment P2

The recombinant mutant *C. utilis* uricase of embodiment P1, wherein the uricase comprises at least one mutation selected from: I180V, I180A, Y165F, V190G, V190A, E51K, Q244K, I132R, V97I, E92N, A87G, D142E, G44A, G128P, A236N, K208A, N213A, S140T, Y253Q, and A84S.

Embodiment P3

The recombinant mutant *C. utilis* uricase of embodiment P1 or P2, wherein the uricase comprises at least one mutation selected from: I180V, I180A, Y165F, V190G, E51K, Q244K, I132R, V97I, E92N, A87G, D142E, and G44A.

Embodiment P4

The recombinant mutant *C. utilis* uricase of any one of embodiments P1-P3, wherein the uricase comprises at least one mutation selected from: I180V, I180A, Y165F, V190G, E51K, I132R, and G44A.

Embodiment P5

The recombinant mutant *C. utilis* uricase of any one of embodiments P1-P4, wherein the uricase comprises at least one mutation selected from: I180V, I180A, Y165F, E51K, I132R, and G44A.

Embodiment P6

The recombinant mutant *C. utilis* uricase of any one of embodiments P1-P5, wherein the uricase comprises at least one mutation selected from: I180V, I180A, Y165F, V190G, E51K, Q244K, and I132R.

Embodiment P7

A recombinant mutant *Candida utilis* uricase comprising at least one (for example, one, two, three, four, five, or six) mutation(s) at a position corresponding to wild type *C. utilis* uricase of SEQ ID NO: 1, wherein the at least one mutation is present at a position selected from position 180, position 165, position 190, position 51, position 132, and position 44.

Embodiment P8

A recombinant mutant *Candida utilis* uricase comprising at least one (for example, one, two, three, four, or five) mutation(s) at a position corresponding to wild type *C. utilis* uricase of SEQ ID NO: 1, wherein the at least one mutation is present at a position selected from position 180, position 165, position 51, position 132, and position 44.

Embodiment P9

A recombinant mutant *Candida utilis* uricase comprising at least one (for example, one, two, three, four, five, or six) mutation(s) at a position corresponding to wild type *C. utilis* uricase of SEQ ID NO: 1, wherein the at least one mutation is present at a position selected from position 180, position 165, position 190, position 51, position 244, and position 132.

Embodiment P10

The recombinant mutant *C. utilis* uricase of any one of embodiments P1-P9, wherein the uricase comprises two, three, four, five, six, seven, or eight mutations.

Embodiment P11

The recombinant mutant *C. utilis* uricase of any one of embodiments P1-P10, wherein the uricase comprises the following substitutions: I180V, Y165F, E51K, I132R, and G44A.

Embodiment P12

The recombinant mutant *C. utilis* uricase of any one of embodiments P1-P10, wherein the uricase comprises the following substitutions: I180A, Y165F, E51K, I132R, and G44A.

Embodiment P13

The recombinant mutant *C. utilis* uricase of any one of embodiments P1-P10, wherein the uricase comprises the following substitutions: I180V, Y165F, V190G, E51K, I132R, and G44A.

Embodiment P14

The recombinant mutant *C. utilis* uricase of any one of embodiments P1-P10, wherein the uricase comprises the following substitutions: I180A, Y165F, V190G, E51K, I132R, and G44A.

Embodiment P15

The recombinant mutant *C. utilis* uricase of any one of embodiments P1-P10, wherein the uricase comprises the following substitutions: I180V and Y165F.

Embodiment P16

The recombinant mutant *C. utilis* uricase of any one of embodiments P1-P10, wherein the uricase comprises the following substitutions: I180V, Y165F, V190G, E51K, Q244K, and I132R.

Embodiment P17

A recombinant mutant *C. utilis* uricase comprising a substitution listed in TABLE 1 or TABLE 2.

Embodiment P18

A recombinant mutant *Candida utilis* uricase having a half-life of at least 35 minutes in the presence of pancreatin.

Embodiment P19

The recombinant mutant *C. utilis* uricase of embodiment P17, wherein the half-life is 35-200 minutes in the presence of pancreatin.

Embodiment P20

The recombinant mutant *C. utilis* uricase of any one of embodiments P1-P19, wherein the uricase has 5-50 fold higher stability in the presence of pancreatin, compared to the wild-type uricase.

Embodiment P21

The recombinant mutant *C. utilis* uricase of embodiment P20, wherein the uricase has 20-30 fold higher stability in the presence of pancreatin, compared to the wild-type uricase.

Embodiment P22

The recombinant mutant *C. utilis* uricase of any one of embodiments P1-P21, wherein the uricase is isolated.

Embodiment P23

The recombinant mutant *C. utilis* uricase of any one of embodiments P1-P22, wherein the uricase is conjugated to a water soluble polymer.

Embodiment P24

The recombinant mutant *C. utilis* uricase of embodiment P23, wherein the uricase is conjugated to polyethylene glycol (PEG).

Embodiment P25

An expression vector comprising a nucleic acid sequence encoding the recombinant mutant *C. utilis* uricase of any one of embodiments P1-P24.

Embodiment P26

The expression vector of embodiment P25, wherein the nucleic acid sequence encoding the recombinant mutant uricase is codon optimized for expression in a heterologous cell.

Embodiment P27

The expression vector of embodiment P26, wherein the heterologous cell is *Escherichia coli*.

Embodiment P28

A cell comprising the expression vector of any one of embodiments P25-P27.

Embodiment P29

The cell of embodiment 28, wherein the cell is *Escherichia coli*.

Embodiment P30

A pharmaceutical composition comprising the recombinant mutant *C. utilis* uricase of any one of embodiments P1-P24.

Embodiment P31

The pharmaceutical composition of embodiment P30, further comprising a pharmaceutically acceptable carrier and/or an excipient.

Embodiment P32

The pharmaceutical composition of embodiment P30 or P31, wherein the composition is formulated as an oral dosage form or a parenteral dosage form.

Embodiment P33

The pharmaceutical composition of embodiment P32, wherein the composition is formulated as an oral dosage form.

Embodiment P34

The pharmaceutical composition of any one of embodiments P30-P33, wherein the composition is a formulated as a powder, granulate, pellet, micropellet, or a minitablet.

Embodiment P35

The pharmaceutical composition of any one of embodiments P30-P34, wherein the composition is encapsulated in a capsule or formulated as a tablet dosage form.

Embodiment P36

The pharmaceutical composition of embodiment P35, wherein the capsule is a hydroxypropyl methylcellulose (HPMC) capsule, soft gelatin capsule, or a hard gelatin capsule.

Embodiment P37

The pharmaceutical composition of embodiment P32, wherein the composition is formulated as a parenteral dosage form.

Embodiment P38

The pharmaceutical composition of embodiment P37, wherein the composition is formulated as an intravenous dosage form.

Embodiment P39

A method of treating a disease or disorder associated with an elevated amount of uric acid in a subject in need thereof, the method comprising administering to the subject an effective amount of the recombinant mutant *C. utilis* uricase of any one of embodiments P1-P24, thereby treating the disease or disorder in the subject.

Embodiment P40

The method of embodiment P39, wherein the disease or disorder is associated with an elevated amount of uric acid in plasma of the subject.

Embodiment P41

A method of treating hyperuricemia in a subject in need thereof, the method comprising administering to the subject an effective amount of the recombinant mutant *C. utilis* uricase of any one of embodiments P1-P24, thereby treating hyperuricemia in the subject.

Embodiment P42

A method of treating gout in a subject in need thereof, the method comprising administering to the subject an effective amount of the recombinant mutant *C. utilis* uricase of any one of embodiments P1-P24, thereby to treat gout in the subject.

Embodiment P43

A method of treating hyperuricemia in a subject in need thereof, the method comprising administering to the subject an effective amount of the pharmaceutical composition of any one of embodiments P30-P38, thereby to treat hyperuricemia in the subject.

Embodiment P44

A method of treating gout in a subject in need thereof, the method comprising administering to the subject an effective amount of the pharmaceutical composition of any one of embodiments P30-P38, thereby to treat gout in the subject.

Embodiment P45

The method of any one of embodiments P39-P44, wherein the recombinant mutant *C. utilis* uricase is administered in combination with a xanthine oxidase inhibitor, a uricosuric, or a combination thereof.

Embodiment P46

The method of embodiment P45, wherein the xanthine oxidase inhibitor is selected from allopurinol and febuxostat.

Embodiment P47

The method of embodiment P45, wherein the uricosuric is selected from probenecid, benzbromarone, losartan and lesinurad.

Embodiment P48

A method of treating hyperuricosuria in a subject in need thereof, the method comprising administering to the subject an effective amount of the recombinant mutant *C. utilis* uricase of any one of embodiments P1-P24, thereby treating hyperuricosuria in the subject.

Embodiment P49

A method of treating hyperuricosuria in a subject in need thereof, the method comprising administering to the subject an effective amount of the pharmaceutical composition of any one of embodiments P30-P38, thereby to treat hyperuricosuria in the subject.

Embodiment P50

The method of embodiment P48 or P49, wherein the recombinant mutant *C. utilis* uricase is administered in combination with a xanthine oxidase inhibitor, a uricosuric, or a combination thereof.

Embodiment P51

The method of embodiment P48 or P49, wherein the recombinant mutant *C. utilis* uricase is administered subsequent to administration of a xanthine oxidase inhibitor, a uricosuric, or a combination thereof.

Embodiment P52

The method of embodiment P50 or P51, wherein the xanthine oxidase inhibitor is selected from allopurinol and febuxostat.

Embodiment P53

The method of embodiment P50 or P51, wherein the uricosuric is selected from probenecid, benzbromarone, losartan and lesinurad.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A recombinant mutant *Candida utilis* uricase comprising two to eight mutations relative to wild type *C. utilis* uricase of SEQ ID NO: 1, wherein at least two of the mutations are selected from: (a) at position 180, isoleucine is substituted by valine or alanine (I180V or I180A), (b) at position 165, tyrosine is substituted by phenylalanine (Y165F), (c) at position 190, valine is substituted by glycine (V190G), (d) at position 51, glutamic acid is substituted by lysine (E51K), (e) at position 244, glutamine is substitute by lysine (Q244K), (f) at position 132, isoleucine is substituted by arginine (I132R), (g) at position 97, valine is substituted by isoleucine (V97I), (h) at position 142, aspartic acid is substituted by glutamic acid (D142E), (i) at position 44, glycine is substituted by alanine (G44A), (j) at position 236, alanine is substituted by asparagine (A236N), (k) at position 196, isoleucine is substituted by leucine (I196L), and (l) at position 285, proline is substituted by serine (P285S).

2. The recombinant mutant *C. utilis* uricase of claim 1, wherein the uricase comprises at least two mutations selected from: I180V, Y165F, E51K, I132R, and G44A.

3. The recombinant mutant *C. utilis* uricase of claim 1, wherein the uricase comprises at least two mutations selected from: I180V, Y165F, V190G, E51K, Q244K, and I132R.

4. The recombinant mutant *C. utilis* uricase of claim 1, wherein the uricase comprises the following substitutions: I180V and Y165F.

5. The recombinant mutant *C. utilis* uricase of claim 1, wherein the uricase comprises the following substitutions: I180V, Y165F, E51K, I132R, and G44A.

6. The recombinant mutant *C. utilis* uricase of claim 1, wherein the uricase comprises the following substitutions: I180A, Y165F, E51K, I132R, and G44A.

7. The recombinant mutant *C. utilis* uricase of claim 1, wherein the uricase comprises the following substitutions: I180V, Y165F, V190G, E51K, I132R, and G44A.

8. The recombinant mutant *C. utilis* uricase of claim 1, wherein the uricase comprises the following substitutions: I180A, Y165F, V190G, E51K, I132R, and G44A.

9. The recombinant mutant *C. utilis* uricase of claim 1, wherein the uricase comprises the following substitutions: I180V, Y165F, V190G, E51K, Q244K, and I132R.

10. The recombinant mutant *C. utilis* uricase of claim 1, wherein the uricase has 5-50 fold higher stability in the presence of pancreatin, compared to the wild-type uricase.

11. The recombinant mutant *C. utilis* uricase of claim 10, wherein the uricase has 20-30 fold higher stability in the presence of pancreatin, compared to the wild-type uricase.

12. The recombinant mutant *C. utilis* uricase of claim 1, wherein the uricase is isolated.

13. The recombinant mutant *C. utilis* uricase of claim 1, wherein the uricase is conjugated to a water soluble polymer.

14. A recombinant mutant *Candida utilis* uricase comprising an amino acid sequence that has at least 99% sequence identity to the amino acid sequence of SEQ ID NO: 2, SEQ ID NO: 3, SEQ ID NO: 4, SEQ ID NO: 5, or SEQ ID NO: 6.

15. The recombinant mutant *C. utilis* uricase of claim 14, wherein the uricase comprises an amino acid sequence that has at least 99% sequence identity to the amino acid sequence of SEQ ID NO: 2.

16. The recombinant mutant *C. utilis* uricase of claim 14, wherein the uricase comprises the amino acid sequence of SEQ ID NO: 2, SEQ ID NO: 3, SEQ ID NO: 4, SEQ ID NO: 5, or SEQ ID NO: 6.

17. The recombinant mutant *C. utilis* uricase of claim 16, wherein the uricase comprises the amino acid sequence of SEQ ID NO: 2.

18. The recombinant mutant *C. utilis* uricase of claim 14, wherein the uricase has 5-50 fold higher stability in the presence of pancreatin, compared to the wild-type uricase.

19. The recombinant mutant *C. utilis* uricase of claim 18, wherein the uricase has 20-30 fold higher stability in the presence of pancreatin, compared to the wild-type uricase.

20. The recombinant mutant *C. utilis* uricase of claim 14, wherein the uricase is isolated.

21. The recombinant mutant *C. utilis* uricase of claim 14, wherein the uricase is conjugated to a water soluble polymer.

22. An expression vector comprising a nucleic acid encoding the recombinant mutant *C. utilis* uricase of claim 14.

23. The expression vector of claim 22, wherein the nucleic acid comprises the nucleotide sequence of SEQ ID NO: 8, SEQ ID NO: 9, SEQ ID NO: 10, SEQ ID NO: 11, SEQ ID NO: 12, or SEQ ID NO: 13.

24. The expression vector of claim 23, wherein the nucleic acid comprises the nucleotide sequence of SEQ ID NO: 13.

25. A pharmaceutical composition comprising the recombinant mutant *C. utilis* uricase of claim 1 and a pharmaceutically acceptable carrier and/or an excipient.

26. A pharmaceutical composition comprising the recombinant mutant *C. utilis* uricase of claim 14 and a pharmaceutically acceptable carrier and/or an excipient.

27. A method of treating a disease or disorder associated with an elevated amount of uric acid in a subject in need thereof, the method comprising administering to the subject an effective amount of a recombinant mutant *Candida utilis* uricase comprising an amino acid sequence that has at least 99% sequence identity to the amino acid sequence of SEQ ID NO: 2, SEQ ID NO: 3, SEQ ID NO: 4, SEQ ID NO: 5, or SEQ ID NO: 6.

28. The method of claim 27, wherein the uricase comprises an amino acid sequence that has at least 99% sequence identity to the amino acid sequence of SEQ ID NO: 2.

29. The method of claim 27, wherein the disease or disorder associated with an elevated amount of uric acid is selected from hyperuricemia, gout, and hyperuricosuria.

30. A recombinant mutant *Candida utilis* uricase expressed from an expression vector comprising the nucleotide sequence of SEQ ID NO: 8, SEQ ID NO: 9, SEQ ID NO: 10, SEQ ID NO: 11, SEQ ID NO: 12, or SEQ ID NO: 13.

* * * * *

SEQUENCE LISTING

<160> NUMBER OF SEQ ID NOS: 13

<210> SEQ ID NO 1
<211> LENGTH: 303
<212> TYPE: PRT
<213> ORGANISM: Candida utilis

<400> SEQUENCE: 1

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
        195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
    290                 295                 300

<210> SEQ ID NO 2
<211> LENGTH: 303
<212> TYPE: PRT
<213> ORGANISM: Artificial Sequence
<220> FEATURE:
<223> OTHER INFORMATION: R2_V17

<400> SEQUENCE: 2

Met Ser Thr Thr Leu Ser Ser Ser Thr Tyr Gly Lys Asp Asn Val Lys
1               5                   10                  15

```
Phe Leu Lys Val Lys Lys Asp Pro Gln Asn Pro Lys Lys Gln Glu Val
             20                  25                  30

Met Glu Ala Thr Val Thr Cys Leu Leu Glu Gly Ala Phe Asp Thr Ser
         35                  40                  45

Tyr Thr Lys Ala Asp Asn Ser Ser Ile Val Pro Thr Asp Thr Val Lys
     50                  55                  60

Asn Thr Ile Leu Val Leu Ala Lys Thr Thr Glu Ile Trp Pro Ile Glu
 65                  70                  75                  80

Arg Phe Ala Ala Lys Leu Ala Thr His Phe Val Glu Lys Tyr Ser His
                 85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Arg Thr Asp Leu Tyr Tyr Lys Arg Ser Gly Asp Tyr Lys
130                 135                 140

Leu Ser Ser Ala Ile Lys Asp Leu Thr Val Leu Lys Ser Thr Gly Ser
145                 150                 155                 160

Met Phe Tyr Gly Phe Asn Lys Cys Asp Phe Thr Thr Leu Gln Pro Thr
                165                 170                 175

Thr Asp Arg Val Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300

<210> SEQ ID NO 3
<211> LENGTH: 303
<212> TYPE: PRT
<213> ORGANISM: Artificial Sequence
<220> FEATURE:
<223> OTHER INFORMATION: R2_V4

<400> SEQUENCE: 3

Met Ser Thr Thr Leu Ser Ser Ser Thr Tyr Gly Lys Asp Asn Val Lys
 1               5                  10                  15

Phe Leu Lys Val Lys Lys Asp Pro Gln Asn Pro Lys Lys Gln Glu Val
             20                  25                  30

Met Glu Ala Thr Val Thr Cys Leu Leu Glu Gly Gly Phe Asp Thr Ser
         35                  40                  45

Tyr Thr Lys Ala Asp Asn Ser Ser Ile Val Pro Thr Asp Thr Val Lys
     50                  55                  60

Asn Thr Ile Leu Val Leu Ala Lys Thr Thr Glu Ile Trp Pro Ile Glu
 65                  70                  75                  80
```

```
Arg Phe Ala Ala Lys Leu Ala Thr His Phe Val Glu Lys Tyr Ser His
                85                  90                  95

Ile Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Phe Asn Lys Cys Asp Phe Thr Thr Leu Gln Pro Thr
                165                 170                 175

Thr Asp Arg Val Leu Ser Thr Asp Val Asp Ala Thr Trp Val Trp Asp
            180                 185                 190

Asn Lys Lys Ile Gly Ser Val Tyr Asp Ile Ala Lys Ala Asp Lys
            195                 200                 205

Gly Ile Phe Asp Asn Val Tyr Asn Gln Ala Arg Glu Ile Thr Leu Thr
        210                 215                 220

Thr Phe Ala Leu Glu Asn Ser Pro Ser Val Gln Asn Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Lys Thr Lys Leu
        290                 295                 300

<210> SEQ ID NO 4
<211> LENGTH: 303
<212> TYPE: PRT
<213> ORGANISM: Artificial Sequence
<220> FEATURE:
<223> OTHER INFORMATION: R2_V79

<400> SEQUENCE: 4

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Arg Thr Asp Leu Tyr Tyr Lys Arg Ser Gly Asp Tyr Lys
        130                 135                 140
```

```
Leu Ser Ser Ala Ile Lys Asp Leu Thr Val Leu Lys Ser Thr Gly Ser
145                 150                 155                 160

Met Phe Tyr Gly Phe Asn Lys Cys Asp Phe Thr Thr Leu Gln Pro Thr
            165                 170                 175

Thr Asp Arg Val Leu Ser Thr Asp Val Asp Ala Thr Trp Val Trp Asp
            180                 185                 190

Asn Lys Lys Ile Gly Ser Val Tyr Asp Ile Ala Lys Ala Asp Lys
            195                 200                 205

Gly Ile Phe Asp Asn Val Tyr Asn Leu Ala Arg Glu Ile Thr Leu Thr
            210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
                245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Ser His Pro Asn
            275                 280                 285

Gly Leu Ile Lys Cys Thr Val Val Arg Lys Glu Lys Thr Lys Leu
            290                 295                 300

<210> SEQ ID NO 5
<211> LENGTH: 303
<212> TYPE: PRT
<213> ORGANISM: Artificial Sequence
<220> FEATURE:
<223> OTHER INFORMATION: R2_V47

<400> SEQUENCE: 5

Met Ser Thr Thr Leu Ser Ser Ser Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
            35                  40                  45

Tyr Thr Lys Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Ile Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Asp Tyr Lys
        130                 135                 140

Leu Ser Ser Ala Ile Lys Asp Leu Thr Val Leu Lys Ser Thr Gly Ser
145                 150                 155                 160

Met Phe Tyr Gly Phe Asn Lys Cys Asp Phe Thr Thr Leu Gln Pro Thr
            165                 170                 175

Thr Asp Arg Val Leu Ser Thr Asp Val Asp Ala Thr Trp Val Trp Asp
            180                 185                 190

Asn Lys Lys Leu Gly Ser Val Tyr Asp Ile Ala Lys Ala Asp Lys
            195                 200                 205
```

Gly Ile Phe Asp Asn Val Tyr Asn Gln Ala Arg Glu Ile Thr Leu Thr
            210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300

<210> SEQ ID NO 6
<211> LENGTH: 303
<212> TYPE: PRT
<213> ORGANISM: Artificial Sequence
<220> FEATURE:
<223> OTHER INFORMATION: R2_V39

<400> SEQUENCE: 6

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Lys Ala Asp Asn Ser Ser Ile Val Pro Thr Asp Thr Val Lys
50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
            85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
            115                 120                 125

Glu Lys Arg Ile Thr Asp Leu Tyr Tyr Lys Arg Ser Gly Glu Tyr Lys
        130                 135                 140

Leu Ser Ser Ala Ile Lys Asp Leu Thr Val Leu Lys Ser Thr Gly Ser
145                 150                 155                 160

Met Phe Tyr Gly Phe Asn Lys Cys Asp Phe Thr Thr Leu Gln Pro Thr
                165                 170                 175

Thr Asp Arg Val Leu Ser Thr Asp Val Asp Ala Thr Trp Val Trp Asp
            180                 185                 190

Asn Lys Lys Ile Gly Ser Val Tyr Asp Ile Ala Lys Ala Ala Asp Lys
            195                 200                 205

Gly Ile Phe Asp Asn Val Tyr Asn Leu Ala Arg Glu Ile Thr Leu Thr
            210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
            245                 250                 255

Tyr Ala Leu Pro Asn Lys His Tyr Phe Leu Ile Asp Leu Lys Trp Lys
            260                 265                 270

Gly Leu Glu Asn Asp Asn Glu Leu Phe Tyr Pro Ser Pro His Pro Asn
        275                 280                 285

Gly Leu Ile Lys Cys Thr Val Val Arg Lys Glu Lys Thr Lys Leu
        290                 295                 300

<210> SEQ ID NO 7
<211> LENGTH: 909
<212> TYPE: DNA
<213> ORGANISM: Candida utilis

<400> SEQUENCE: 7

| | |
|---|---|
| atgtcgacga ccctgagcag cagcacctat ggcaaagata atgtgaaatt tctgaaagtc | 60 |
| aaaaaagacc cgcagaaccc taagaaacaa gaggtcatgg aagcgaccgt tacgtgtctg | 120 |
| ctggaaggcg gcttcgacac cagctatacc gaagcggata ttcctccat cgttccgacc | 180 |
| gatacggtca gaacaccat tctggttctg gccaagacca cggaaatctg gccaattgag | 240 |
| cgcttcgccg cgaaactggc gacccatttc gttgagaagt acagccacgt gagcggcgtg | 300 |
| agcgttaaaa ttgttcagga tcgttgggtc aaatatgccg tggatggtaa gccgcatgac | 360 |
| cacagctta ttcacgaggg tggcgagaag cgtatcactg acctgtatta caagcgcagc | 420 |
| ggtgactaca aattgagcag cgcaatcaaa gacctgacgg tcctgaaaag caccggttct | 480 |
| atgttttacg gttacaataa gtgcgacttt acgacgctcc aaccgactac ggaccgtatc | 540 |
| ctgtctaccg atgtagacgc gacctgggtc tgggataaca agaaaattgg cagcgtgtac | 600 |
| gatattgcga aagccgctga caagggtatc ttcgacaacg tctataatca agcgcgtgag | 660 |
| atcaccctga ccacgtttgc tctggagaat tccccgagcg ttcaggcgac catgtttaac | 720 |
| atggcaacgc agattttgga aaaggcatgt agcgtgtaca gcgtgagcta tgcattgccg | 780 |
| aataagcact acttcctgat tgatctgaag tggaagggtc tggagaacga taacgaactg | 840 |
| ttctatccga gcccgcaccc gaatggtctg atcaagtgca ccgttgtgcg taaagaaaag | 900 |
| actaaactg | 909 |

<210> SEQ ID NO 8
<211> LENGTH: 909
<212> TYPE: DNA
<213> ORGANISM: Artificial Sequence
<220> FEATURE:
<223> OTHER INFORMATION: R2_V17

<400> SEQUENCE: 8

| | |
|---|---|
| atgtcgacga ccctgagcag cagcacctat ggcaaagata atgtgaaatt tctgaaagtc | 60 |
| aaaaaagacc cgcagaaccc taagaaacaa gaggtcatgg aagcgaccgt tacgtgtctg | 120 |
| ctggaaggcg cgttcgacac cagctatacc aaagcggata ttcctccat cgttccgacc | 180 |
| gatacggtca gaacaccat tctggttctg gccaagacca cggaaatctg gccaattgag | 240 |
| cgcttcgccg cgaaactggc gacccatttc gttgagaagt acagccacgt gagcggcgtg | 300 |
| agcgttaaaa ttgttcagga tcgttgggtc aaatatgccg tggatggtaa gccgcatgac | 360 |
| cacagctta ttcacgaggg tggcgagaag cgtcgtactg acctgtatta caagcgcagc | 420 |
| ggtgactaca aattgagcag cgcaatcaaa gacctgacgg tcctgaaaag caccggttct | 480 |
| atgttttacg gtttcaataa gtgcgacttt acgacgctcc aaccgactac ggaccgtgtt | 540 |
| ctgtctaccg atgtagacgc gacctgggtc tgggataaca agaaaattgg cagcgtgtac | 600 |
| gatattgcga aagccgctga caagggtatc ttcgacaacg tctataatca agcgcgtgag | 660 |

| atcaccctga ccacgtttgc tctggagaat tccccgagcg ttcaggcgac catgtttaac | 720 |
| atggcaacgc agattttgga aaaggcatgt agcgtgtaca gcgtgagcta tgcattgccg | 780 |
| aataagcact acttcctgat tgatctgaag tggaagggtc tggagaacga taacgaactg | 840 |
| ttctatccga gcccgcaccc gaatggtctg atcaagtgca ccgttgtgcg taaagaaaag | 900 |
| actaaactg | 909 |

<210> SEQ ID NO 9
<211> LENGTH: 909
<212> TYPE: DNA
<213> ORGANISM: Artificial Sequence
<220> FEATURE:
<223> OTHER INFORMATION: R2_V4

<400> SEQUENCE: 9

| atgtcgacga ccctgagcag cagcacctat ggcaaagata atgtgaaatt tctgaaagtc | 60 |
| aaaaaagacc cgcagaaccc taagaaacaa gaggtcatgg aagcgaccgt tacgtgtctg | 120 |
| ctggaaggcg gcttcgacac cagctatacc aaagcggata attcctccat cgttccgacc | 180 |
| gatacggtca agaacaccat tctggttctg gccaagacca cggaaatctg gccaattgag | 240 |
| cgcttcgccg cgaaactggc gacccatttc gttgagaagt acagccacat cagcggcgtg | 300 |
| agcgttaaaa ttgttcagga tcgttgggtc aaatatgccg tggatggtaa gccgcatgac | 360 |
| cacagcttta ttcacgaggg tggcgagaag cgtatcactg acctgtatta caagcgcagc | 420 |
| ggtgactaca aattgagcag cgcaatcaaa gacctgacgg tcctgaaaag caccggttct | 480 |
| atgtttacg gtttcaataa gtcgactttt acgacgctcc aaccgactac ggaccgtgtt | 540 |
| ctgtctaccg atgtagacgc gacctgggtc tgggataaca agaaaattgg cagcgtgtac | 600 |
| gatattgcga agccgctga caagggtatc ttcgacaacg tctataatca agcgcgtgag | 660 |
| atcaccctga ccacgtttgc tctggagaat tccccgagcg ttcagaacac catgtttaac | 720 |
| atggcaacgc agattttgga aaaggcatgt agcgtgtaca gcgtgagcta tgcattgccg | 780 |
| aataagcact acttcctgat tgatctgaag tggaagggtc tggagaacga taacgaactg | 840 |
| ttctatccga gcccgcaccc gaatggtctg atcaagtgca ccgttgtgcg taaagaaaag | 900 |
| actaaactg | 909 |

<210> SEQ ID NO 10
<211> LENGTH: 909
<212> TYPE: DNA
<213> ORGANISM: Artificial Sequence
<220> FEATURE:
<223> OTHER INFORMATION: R2_V79

<400> SEQUENCE: 10

| atgtcgacga ccctgagcag cagcacctat ggcaaagata atgtgaaatt tctgaaagtc | 60 |
| aaaaaagacc cgcagaaccc taagaaacaa gaggtcatgg aagcgaccgt tacgtgtctg | 120 |
| ctggaaggcg gcttcgacac cagctatacc gaagcggata attcctccat cgttccgacc | 180 |
| gatacggtca agaacaccat tctggttctg gccaagacca cggaaatctg gccaattgag | 240 |
| cgcttcgccg cgaaactggc gacccatttc gttgagaagt acagccacgt gagcggcgtg | 300 |
| agcgttaaaa ttgttcagga tcgttgggtc aaatatgccg tggatggtaa gccgcatgac | 360 |
| cacagcttta ttcacgaggg tggcgagaag cgtcgtactg acctgtatta caagcgcagc | 420 |
| ggtgactaca aattgagcag cgcaatcaaa gacctgacgg tcctgaaaag caccggttct | 480 |
| atgtttacg gtttcaataa gtcgactttt acgacgctcc aaccgactac ggaccgtgtt | 540 |

```
ctgtctaccg atgtagacgc gacctgggtc tgggataaca agaaaattgg cagcgtgtac    600
gatattgcga aagccgctga caagggtatc ttcgacaacg tctataatct ggcgcgtgag    660
atcaccctga ccacgtttgc tctggagaat tccccgagcg ttcaggcgac catgtttaac    720
atggcaacgc agattttgga aaaggcatgt agcgtgtaca gcgtgagcta tgcattgccg    780
aataagcact acttcctgat tgatctgaag tggaagggtc tggagaacga taacgaactg    840
ttctatccga gcagccaccc gaatggtctg atcaagtgca ccgttgtgcg taaagaaaag    900
actaaactg                                                            909
```

<210> SEQ ID NO 11
<211> LENGTH: 909
<212> TYPE: DNA
<213> ORGANISM: Artificial Sequence
<220> FEATURE:
<223> OTHER INFORMATION: R2_V47

<400> SEQUENCE: 11

```
atgtcgacga ccctgagcag cagcacctat ggcaaagata atgtgaaatt tctgaaagtc     60
aaaaaagacc cgcagaaccc taagaaacaa gaggtcatgg aagcgaccgt tacgtgtctg    120
ctggaaggcg gcttcgacac cagctatacc aaagcggata attcctccat cgttccgacc    180
gatacggtca agaacaccat tctggttctg gccaagacca cggaaatctg gccaattgag    240
cgcttcgccg cgaaactggc gacccatttc gttgagaagt acagccacat cagcggcgtg    300
agcgttaaaa ttgttcagga tcgttgggtc aaatatgccg tggatggtaa gccgcatgac    360
cacagcttta ttcacgaggg tggcgagaag cgtatcactg acctgtatta caagcgcagc    420
ggtgactaca aattgagcag cgcaatcaaa gacctgacgg tcctgaaaag caccggttct    480
atgttttacg gtttcaataa gtcgactttt acgacgctcc aaccgactac ggaccgtgtt    540
ctgtctaccg atgtagacgc gacctgggtc tgggataaca agaaactggg cagcgtgtac    600
gatattgcga aagccgctga caagggtatc ttcgacaacg tctataatca agcgcgtgag    660
atcaccctga ccacgtttgc tctggagaat tccccgagcg ttcaggcgac catgtttaac    720
atggcaacgc agattttgga aaaggcatgt agcgtgtaca gcgtgagcta tgcattgccg    780
aataagcact acttcctgat tgatctgaag tggaagggtc tggagaacga taacgaactg    840
ttctatccga gcccgcaccc gaatggtctg atcaagtgca ccgttgtgcg taaagaaaag    900
actaaactg                                                            909
```

<210> SEQ ID NO 12
<211> LENGTH: 909
<212> TYPE: DNA
<213> ORGANISM: Artificial Sequence
<220> FEATURE:
<223> OTHER INFORMATION: R2_V39

<400> SEQUENCE: 12

```
atgtcgacga ccctgagcag cagcacctat ggcaaagata atgtgaaatt tctgaaagtc     60
aaaaaagacc cgcagaaccc taagaaacaa gaggtcatgg aagcgaccgt tacgtgtctg    120
ctggaaggcg gcttcgacac cagctatacc aaagcggata attcctccat cgttccgacc    180
gatacggtca agaacaccat tctggttctg gccaagacca cggaaatctg gccaattgag    240
cgcttcgccg cgaaactggc gacccatttc gttgagaagt acagccacgt gagcggcgtg    300
agcgttaaaa ttgttcagga tcgttgggtc aaatatgccg tggatggtaa gccgcatgac    360
```

```
cacagcttta ttcacgaggg tggcgagaag cgtatcactg acctgtatta caagcgcagc      420
ggtgagtaca aattgagcag cgcaatcaaa gacctgacgg tcctgaaaag caccggttct      480
atgttttacg gtttcaataa gtgcgacttt acgacgctcc aaccgactac ggaccgtgtt      540
ctgtctaccg atgtagacgc gacctgggtc tgggataaca agaaaattgg cagcgtgtac      600
gatattgcga aagccgctga caagggtatc ttcgacaacg tctataatct ggcgcgtgag      660
atcaccctga ccacgtttgc tctggagaat tccccgagcg ttcaggcgac catgtttaac      720
atggcaacgc agattttgga aaaggcatgt agcgtgtaca gcgtgagcta tgcattgccg      780
aataagcact acttcctgat tgatctgaag tggaagggtc tggagaacga taacgaactg      840
ttctatccga gcccgcaccc gaatggtctg atcaagtgca ccgttgtgcg taaagaaaag      900
actaaactg                                                              909

<210> SEQ ID NO 13
<211> LENGTH: 909
<212> TYPE: DNA
<213> ORGANISM: Artificial Sequence
<220> FEATURE:
<223> OTHER INFORMATION: Codon-optimized nucleic acid sequence encoding
      a mutant Candida utilis uricase

<400> SEQUENCE: 13
atgagcacca cactgagcag cagcacctat ggtaaagata atgtgaaatt cctgaaagtg       60
aaaaaagatc cgcagaaccc gaaaaaacaa gaagttatgg aagcaaccgt tacctgtctg      120
ctggaaggtg catttgatac cagctatacc aaagcagata atagcagcat tgttccgacc      180
gataccgtga aaataccat tctggttctg gcaaaaacca ccgaaatttg gccgattgaa       240
cgttttgcag ccaaactggc aacccatttt gttgagaaat attctcatgt tagcggtgtg      300
agcgttaaaa ttgttcagga tcgttgggtt aaatatgccg ttgatggtaa accgcatgat      360
cacagcttta ttcatgaagg tggtgaaaaa cgtcgtaccg atctgtatta caaacgtagc      420
ggtgattata aactgtccag cgcaattaaa gatctgaccg ttctgaaaag caccggcagc      480
atgttttatg gttttaacaa atgcgatttc acaaccctgc agccgaccac cgatcgtgtt      540
ctgagcaccg atgttgatgc aacctgggtt tgggataata agaaaattgg tagcgtgtac      600
gatattgcca aagcagcaga taaaggcatc ttcgataatg tgtataatca ggcacgtgaa      660
attaccctga ccacctttgc actggaaaat agcccgagcg ttcaggcaac catgtttaat      720
atggcgaccc agattctgga aaaagcgtgt agcgtttata gcgttagcta tgcactgccg      780
aacaaacact attttctgat tgacctgaaa tggaagggcc ttgaaaatga taacgaactg      840
ttttatccga gtccgcatcc gaatggtctg attaaatgta ccgttgtgcg taaagagaaa      900
accaaactg                                                              909
```